United States Patent
Lee et al.

(10) Patent No.: US 11,911,106 B2
(45) Date of Patent: Feb. 27, 2024

(54) DEVICE AND METHOD FOR REDUCING EYE OPACITY

(71) Applicant: KOREA PHOTONICS TECHNOLOGY INSTITUTE, Gwangju (KR)

(72) Inventors: Kwanghoon Lee, Anyang-si (KR); Sungguk Chun, Gwangju (KR); Seonkyu Yoon, Gwangju (KR); Seon Man Kim, Gwangju (KR)

( * ) Notice: Subject to any disclaimer, the term of this patent is extended or adjusted under 35 U.S.C. 154(b) by 459 days.

(21) Appl. No.: 16/719,971

(22) Filed: Dec. 18, 2019

(65) Prior Publication Data
US 2021/0003861 A1 Jan. 7, 2021

(30) Foreign Application Priority Data

Jul. 5, 2019 (KR) .................. 10-2019-0081418
Jul. 5, 2019 (KR) .................. 10-2019-0081475
Jul. 5, 2019 (KR) .................. 10-2019-0081506

(51) Int. Cl.
*A61B 3/117* (2006.01)
*A61B 3/10* (2006.01)
*G02C 7/02* (2006.01)

(52) U.S. Cl.
CPC .......... *A61B 3/1176* (2013.01); *A61B 3/1015* (2013.01); *G02C 7/02* (2013.01); *G02C 2202/10* (2013.01)

(58) Field of Classification Search
CPC ..................................... G02C 7/083
USPC ....................................... 351/205
See application file for complete search history.

(56) References Cited

U.S. PATENT DOCUMENTS

| 4,300,818 | A | * | 11/1981 | Schachar | G02C 7/083 351/158 |
| 8,488,851 | B2 | * | 7/2013 | Artal Soriano | A61B 3/101 382/128 |
| 10,690,940 | B2 | * | 6/2020 | Pugh | G02C 7/083 |
| 10,835,118 | B2 | * | 11/2020 | Hoggarth | G02C 7/081 |
| 10,932,902 | B2 | * | 3/2021 | Reedy | G02C 7/083 |
| 11,022,818 | B2 | * | 6/2021 | Gutierrez | G02C 7/101 |
| 2010/0195876 | A1 | * | 8/2010 | Artal Soriano | A61B 3/1176 382/128 |
| 2013/0261744 | A1 | | 10/2013 | Gupta et al. | |
| 2019/0107736 | A1 | * | 4/2019 | Gutierrez | G02C 7/04 |

(Continued)

FOREIGN PATENT DOCUMENTS

| EP | 2997940 A2 | 3/2016 | |
| JP | 2003052631 A | * 2/2003 | ............... A16B 3/12 |
| JP | 2005-118076 A | 5/2005 | |

(Continued)

OTHER PUBLICATIONS

George O. Reynolds, Joel L. Zuckerman, William A. Dyes, David Miller, "Holographic Phase Compensation Techniques Applied to Human Cataracts," Opt. Eng. 12(1) 120123 (Feb. 1, 1973) https://doi.org/10.1117/12.7971624 (Year: 1973).*

(Continued)

*Primary Examiner* — Zachary W Wilkes
(74) *Attorney, Agent, or Firm* — ANTONIO HA & U.S. PATENT, LLC

(57) ABSTRACT

An optical modulator is disposed in front of an eye along a direction in which light enters the eye to modulate the properties of light depending on the degree of opacity of the eye.

7 Claims, 20 Drawing Sheets

(56) References Cited

U.S. PATENT DOCUMENTS

2020/0100670 A1* 4/2020 Hoggarth ............... G02C 7/081

FOREIGN PATENT DOCUMENTS

| JP | 2013-532010 A | 8/2013 |
|----|---------------|--------|
| KR | 10-2010-0114133 | 10/2010 |

OTHER PUBLICATIONS

Reynolds, George O. "Letter to the Editor: Phase Aberration Balancing of Simulated Cataracts in the Reflection Mode." Optical Engineering, vol. 12, No. 2, 1973, pp. 80-82 (Year: 1973).*

Pablo Artal, Augusto Arias, and Enrique Fernández "Wavefront shaping to correct intraocular scattering", Proc. SPIE 10502, Adaptive Optics and Wavefront Control for Biological Systems IV, 105020Q (Feb. 23, 2018); https://doi.org/10.1117/12.2290388 (Year: 2018).*

Arias, Augusto, and Pablo Artal. "Wavefront-Shaping-Based Correction of Optically Simulated Cataracts." Optica, vol. 7, No. 1, 2020, pp. 22-27., https://doi.org/10.1364/optica.7.000022 (Year: 2020).*

I. M. Vellekoop and A. P. Mosk, "Focusing coherent light through opaque strongly scattering media," Opt. Lett. 32, 2309-2311 (2007) (Year: 2007).*

A. Arias, E. Fernández, and P. Artal, "Optical correction of the effects of cataracts," in Latin America Optics and Photonics Conference, OSA Technical Digest (Optica Publishing Group, 2018), paper W2C.2 (Year: 2018).*

English Specification of JP2013-532010A.
English Specification of 10-2010-0114133.
English Specification of JP2005-118076A.
English Specification of JP2003-052631A.

* cited by examiner

DEVICE AND METHOD FOR REDUCING EYE OPACITY

STATEMENT OF GOVERNMENT SUPPORT

This work was supported by Institute of Information & communications Technology Planning & Evaluation (IITP) grant funded by the Korea government (MSIT) (No. 2021-0-00343, Development of metrology for the properties of reconstructed digital hologram's space and color).

CROSS-REFERENCE TO RELATED APPLICATION(S)

This application is based on and claims priority under 35 U.S.C. 119 to Korean Patent Application Nos. 10-2019-0081418, filed on May 7, 2019, 10-2019-0081475, filed on May 7, 2019, and 10-2019-0081506, filed on May 7, 2019, in the Korean Intellectual Property Office, the disclosure of which is herein incorporated by reference in its entirety.

TECHNICAL FIELD

Embodiments of the disclosure relate to a device and method for reducing eye opacity.

DESCRIPTION OF RELATED ART

The description of the Discussion of Related Art section merely provides information that may be relevant to embodiments of the disclosure but should not be appreciated as necessarily constituting the prior art.

Eyes are organs of the visual system to perceive the color, size, shape, or distance of external objects. They receive visible light coming from the outside, forming images on the retina. The observer recognizes the features of an external object as clear or cloudy depending on the quality of the image formed on the retina. The eye may be divided into its front and back segments. The front segment consists of the cornea, the aqueous humour, the iris, and the front of the lens, and the back segment consists of the back of the lens, the vitreous chamber, and the retina surface. Light incident from the outside to the eye is refracted while passing through the front and back segments and reaches the retina, forming an image. "Normal" visual acuity (in central, i.e. foveal vision) is frequently considered to be what was defined by Herman Snellen as the ability to recognize an optotype when it subtended 5 minutes of arc, that is Snellen's chart 6/6 metre, 20/20 feet, 1.00 decimal or 0.0 log MAR. The front and back segments naturally lose their functionality as they age. Foreign bodies may enter the cornea and the lens, causing corneal opacity and cataracts. These disorders scatter light coming from the outside, deteriorating the quality of an image forming on the retina. If left untreated, cataracts may cause continual loss of vision, eventually leading to total blindness. Cataracts, a major cause of blindness, are very often to elderly people in their sixties.

The only way to treat cataracts known as of today is surgery that replaces the defected lens with an artificial lens. Such a surgical way is inevitably accompanied by eye incision which
is not only very risky but also may leave aftereffects or side effects, even serious post-surgery symptoms unless treated well after surgery.

Thus, a need exists for treating eye opacity or cloudiness, such as corneal opacities or cataracts, at their early stage or before performing surgery.

SUMMARY

An object of the disclosure is to provide an optical modulator and a light modulation method, wherein the optical modulator is disposed in front of or in contact with the eye to modulate the properties of light, thereby relatively reducing the degree of opacity of the front segment including the lens and hence increasing the quality of image formation on the retina.

Another object of the disclosure is to provide an optical modulator and a light modulation method, wherein the optical modulator is disposed in front of or in contact with the eye to actively modulate the properties of light according to the properties of light entering the eye or according to an external control signal.

Another object of the disclosure is to provide an optical modulator and a light modulation method, wherein the optical modulator is disposed in contact with the eye to modulate the properties of light, thereby relatively reducing the degree of opacity of the front segment including the lens and hence increasing the quality of image formation on the retina.

Another object of the disclosure is to provide an optical modulator and a light modulation method, wherein the optical modulator is disposed in contact with the eye to actively modulate the properties of light according to an external control signal.

According to an embodiment, an optical modulator is disposed in front of an eye along a direction in which light enters the eye. The optical modulator may modulate a property of the light depending on a degree of opacity of the eye.

The degree of opacity of the eye may be varied by a foreign body in the eye or depending on a degree of refraction or focusing of the light.

The property of the light may include a phase of the light or a strength of the light.

The optical modulator may be implemented as a light modulator.

There is provided a method of modulating light performed by an optical modulator disposed in front of an eye along a direction in which light enters the eye. The optical modulator may modulate a property of the light depending on a degree of opacity of the eye.

The degree of opacity of the eye may be varied by a foreign body in the eye or depending on a degree of refraction or focusing of the light.

The property of the light may include a phase of the light or a strength of the light.

An optical modulator includes a sensor sensing a property of light entering an eye or a property of light reflected by the eye, a memory storing a property of each light ray and an optimal modulation property of a light modulator according the property of the light ray, with the property of the light matched with the optimal modulation property, a controller analyzing the property of the light sensed by the sensor, selecting the optimal modulation property of the light modulator in the memory, and controlling the light modulator to have the selected modulation property, and the light modulator having a modulation property according to control of the controller and modulating the property of the light entering the eye.

The property of the light may include a phase of the light, a strength of the light, or an incident direction of the light.

The sensor and the light modulator may be disposed in front of the eye along a direction in which the light enters the eye.

The controller may control the modulation property of the light modulator by transferring power corresponding to the modulation property of the light modulator to the light modulator.

A method of modulating light includes detecting a property of light entering an eye and a property of light reflected by the eye, analyzing the property of the light detected by the sensor to select an optimal modulation property of a light modulator according to the detected property, controlling the light modulator to have the selected modulation property, and modulating the property of the light entering the eye.

The property of the light may include a phase of the light, a strength of the light, or an incident direction of the light.

The modulation property of the light modulator may be controlled by transferring power corresponding to the modulation property of the light modulator to the light modulator.

An optical modulation pattern is disposed in front of an eye along a direction in which light enters the eye. The optical modulation pattern may modulate a property of the light depending on a degree of opacity of the eye.

According to an embodiment, a device for detecting the degree of eye opacity includes a first polarizer reflecting only a preset polarization component of light entering the eye, a second polarizer disposed between the first polarizer and the eye to reflect only the preset polarization component of light reflected by the eye, a wave plate between the second polarizer and the eye to shift the phase of light passing through the second polarizer or the phase of light reflected by the eye, a reflector light reflected by one of the first polarizer and the second polarizer in the same direction as light reflected by the other of the first polarizer and the second polarizer, and a detector detecting interfering light of the light reflected by the first polarizer and the light reflected by the second polarizer.

The light entering the eye has only a polarization component with a phase difference of 90 degrees from the preset polarization component while or after passing through the first polarizer and the second polarizer.

The wave plate shifts the phase of the light entering the eye by 45 degrees and shifts the phase of light reflected by the eye by 45 degrees
so that the light reflected by the eye has the preset polarization component.

According to an embodiment, a method of detecting the degree of eye opacity includes first reflecting only a preset polarization component of light entering the eye, shifting the phase of the light entering the eye or the phase of light reflected by the eye, second reflecting only the preset polarization component of the light reflected by the eye, allowing a direction of one of the first-reflected light and the second-reflected light to be identical to a direction of the other of the first-reflected light and the second-reflected light, and detecting interfering light of the first-reflected light and the second-reflected light.

The light entering the eye has only a polarization component with a phase difference of 90 degrees from the preset polarization component while or after first-reflecting or second-reflecting.

The light reflected by the eye has the preset polarization component while or after passing the phase-shifting two times.

According to an embodiment, an eye opacity reducing device includes a light source emitting light to the eye, an optical system leading to interference between light entering the eye and light reflected by the eye, a memory storing interference information for interfering light between light entering a reference eye and light reflected by the reference eye, a detector detecting the interfering light generated by the optical system, and a determining unit comparing the interference information generated by the optical system with the interference information detected by the detector to determine whether an error or difference between the two pieces of interference information falls within a preset error range.

The light source emits a near infrared (IR) wavelength range of light.

The detector detects the strength (or intensity) of the interfering light.

The determining unit compares the strength of the interfering light detected by the detector with the strength of the interfering light for the reference eye stored in the memory, determining whether the difference or error in strength between the two interfering light rays falls within a preset error range.

According to an embodiment, a method of reducing the degree of eye opacity by selecting a component of reducing the degree of eye opacity includes emitting light to the eye, allowing light entering the eye to interfere with light reflected by the eye, detecting interference information for the interfering light, and comparing the detected interference information with interference information for interfering light for a reference eye, determining whether an error or difference between the two pieces of interference information falls within an error range.

Emitting the light to the eye includes emitting a near infrared (IR) wavelength range of light.

Detecting the interference information includes detecting the strength (or intensity) of the interfering light.

According to an embodiment, an optical modulator is disposed in contact with the eye along a direction in which light enters the eye to modulate the properties of light entering the eye depending on the degree of eye opacity.

The optical modulator is implemented in the size of the pupil of the eye.

The optical modulator is implemented as a contact lens.

The properties of light include the incident direction, strength or intensity, or phase of the light.

According to an embodiment, there is provided a method performed by an optical modulator disposed in contact with the eye along a direction in which light enters the eye to modulate the properties of light entering the eye depending on the degree of eye opacity.

The degree of opacity of the eye is varied by a foreign body in the eye or depending on a degree of refraction or focusing of the light.

The properties of light include the incident direction, strength or intensity, or phase of the light.

According to an embodiment, an optical modulator includes a communication unit receiving a control signal regarding an optical modulation property from the outside, a light modulator modulating the property of light entering the eye and actively varying the optical modulation property, and a controller analyzing the control signal to control the optical modulation property of the light modulator according to the control signal.

The optical modulator is implemented as a solar cell.

The optical modulator further includes a battery supplying power to operate the components in the optical modulator.

The battery stores electric energy obtained by the solar cell.

According to an embodiment, a method of modulating light by an optical modulator includes receiving a control signal regarding a modulation property from the outside and modulating the properties of the optical modulator according to the received control signal.

The optical modulator is implemented as a solar cell.

The optical modulator further includes a battery to store electric energy obtained by the solar cell to provide power necessary for receiving the control signal and modulating the light.

As described above, according to the embodiments, the optical modulator is disposed in front of or in contact with the eye to modulate the properties of light entering the eye, thus reducing the degree of eye opacity and hence enhancing the symptom of, e.g., corneal opacity or cataracts without the need for surgery.

The embodiments may actively inverse-modulate the properties of light scattered in the eye via the operation of detecting the properties of the scattered light, thereby minimizing the opacity symptom.

The embodiments may actively inverse-modulate the properties of scattered light according to a control signal from the outside, thereby minimizing the opacity symptom for each patient.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

DETAILED DESCRIPTION OF EXEMPLARY EMBODIMENTS

Various changes may be made to the disclosure, and the disclosure may come with a diversity of embodiments. Some embodiments of the disclosure are shown and described in connection with the drawings. However, it should be appreciated that the disclosure is not limited to the embodiments, and all changes and/or equivalents or replacements thereto also belong to the scope of the disclosure. Similar reference denotations are used to refer to similar elements throughout the drawings.

The terms "first" and "second" may be used to describe various components, but the components should not be limited by the terms. The terms are used to distinguish one component from another. For example, a first component may be denoted a second component, and vice versa without departing from the scope of the disclosure. The term "and/or" may denote a combination(s) of a plurality of related items as listed or any of the items.

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when a component is "directly connected to" or "directly coupled to" another component, no other intervening components may intervene therebetween.

The terms as used herein are provided merely to describe some embodiments thereof, but not to limit the disclosure. As used herein, the singular forms "a," "an," and "the" are intended to include the plural forms as well, unless the context clearly indicates otherwise. As used herein, the term "comprise," "include," or "have" should be appreciated not to preclude the presence or addability of features, numbers, steps, operations, components, parts, or combinations thereof as set forth herein.

Unless otherwise defined, all terms including technical and scientific terms used herein have the same meaning as commonly understood by one of ordinary skill in the art to which the embodiments of the disclosure belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The components, processes, steps, or methods according to embodiments of the disclosure may be shared as long as they do not technically conflict with each other.

Figure 1:
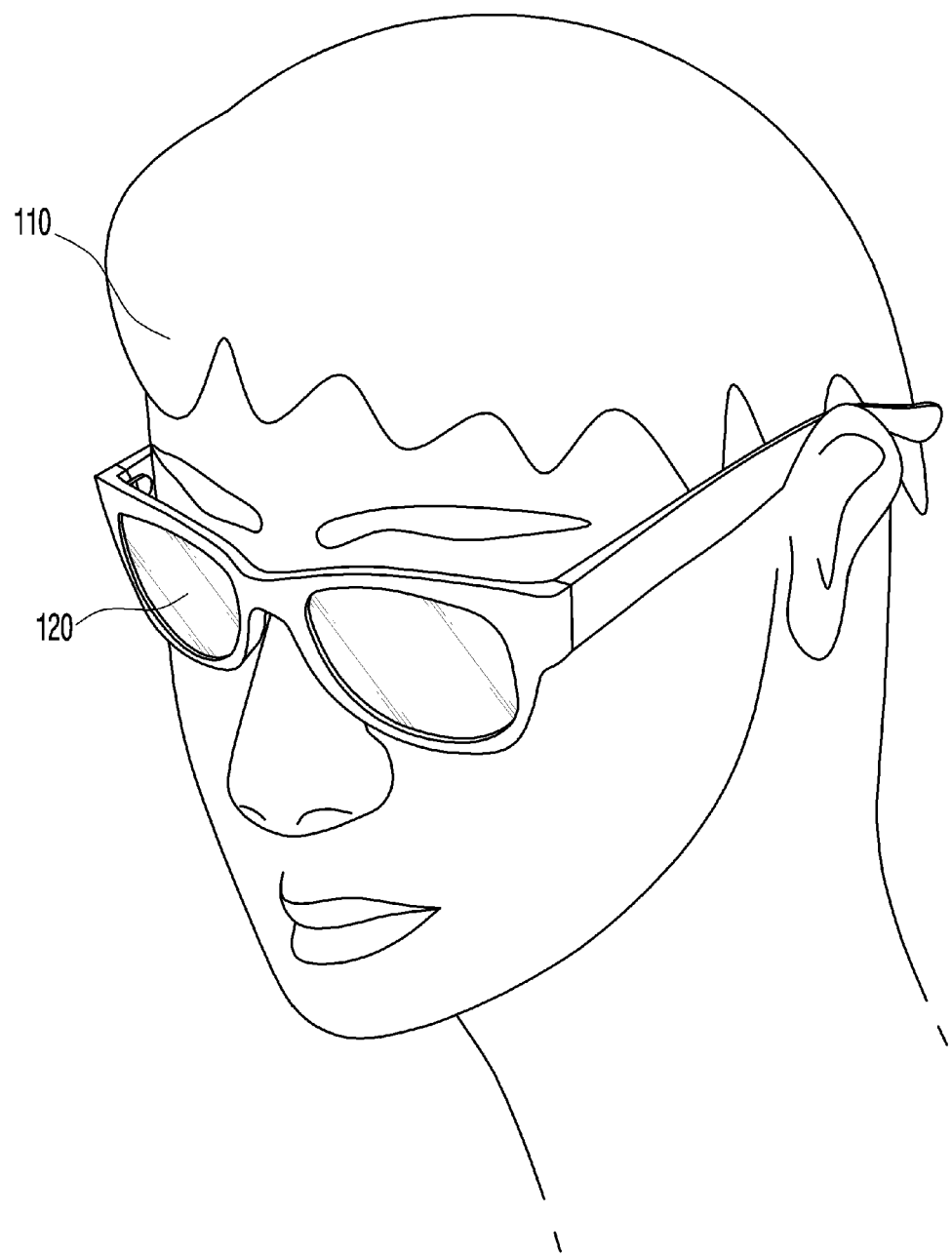
FIG. 1 is a perspective view illustrating an example product printed with an optical pattern determined from an optical modulator according to a first embodiment of the disclosure.

FIG. 1 is a perspective view illustrating an example product printed with an optical pattern determined from an optical modulator according to a first embodiment of the disclosure.

When light enters the eye of the patient 110 suffering from eye opacity (or clouded eye), the light may be scattered by the factor causing the eye opacity, failing to be precisely focused on the retina. Thus, the patient 110 sees external objects as blurred or cloudy.

To mitigate such symptom, an optical modulator 120 is disposed in front of the patient's eyes. The optical modulator 120 is positioned ahead of the eyes of the patient 110 suffering from eye opacity, modulating the properties of the incident light depending on the degree of eye opacity. The properties of light modulated by the optical modulator 120 may include the phase, strength, or intensity of the light. The optical modulator 120 modulates the properties of light entering the eyes from ahead of the patient's eyes depending on the degree of eye opacity, allowing the modulated light to be normally focused on the retina while passing through the clouded eye, particularly, clouded lens.

The optical modulator 120 may be implemented as an optical device capable of modulating or changing the properties of light, such as a light modulator (LM) or spatial light modulator (SLM). For example, the optical modulator 120 may be implemented as a reflective optical modulator, such as a digital mirror device (DMD), to modulate the properties, e.g., direction or strength of light, or the optical modulator 120 may be implemented as a transmissive optical modulator to modulate all of the properties, e.g., direction, strength, and phase, of light. When the optical modulator 120 is implemented as a reflective optical modulator, the optical modulator 120 may quickly perform light modulation. When the optical modulator 120 is implemented as a transmissive optical modulator, the optical modulator 120 may perform light modulation more specifically and precisely.

Figure 2:
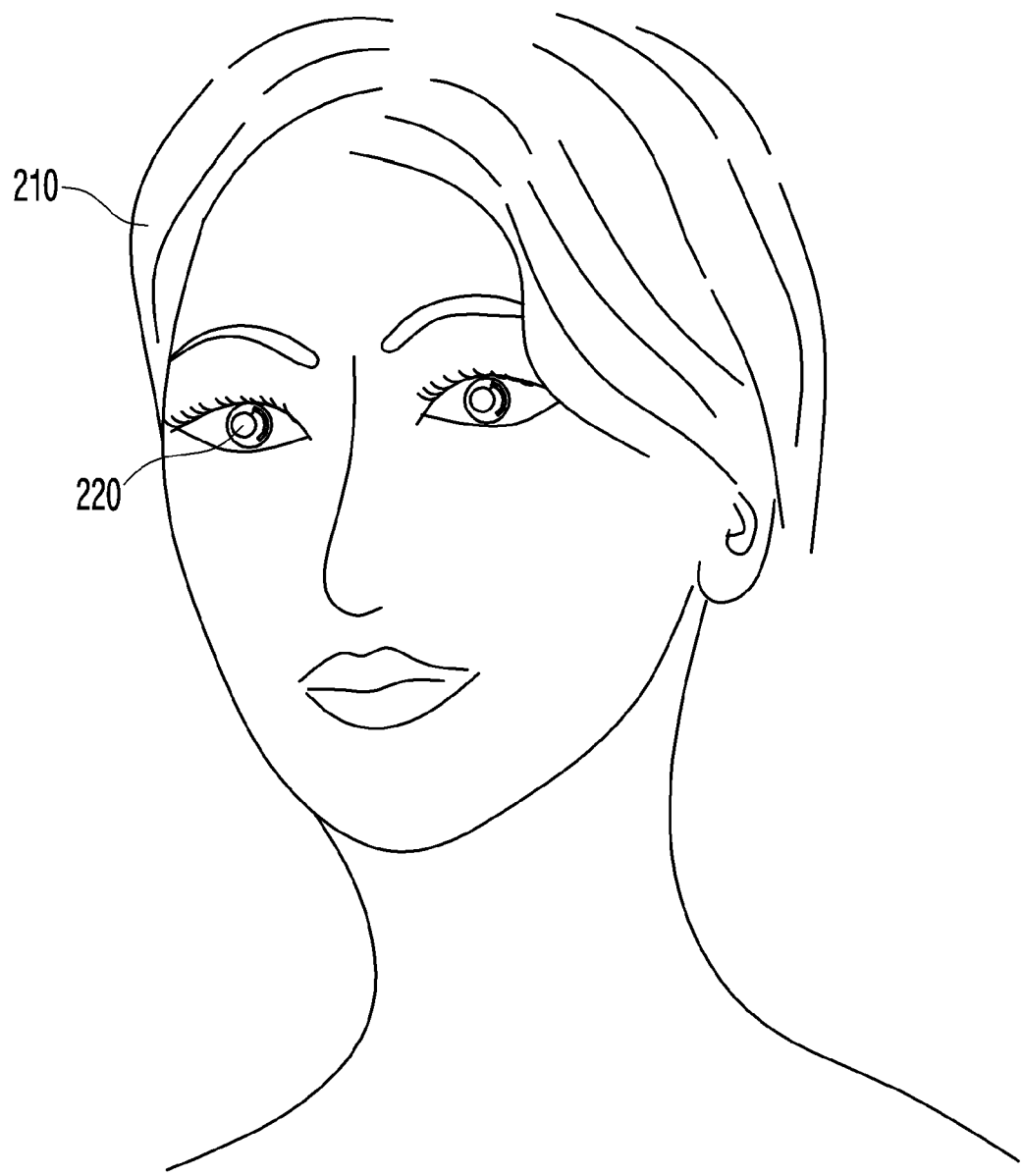
FIG. 2 is a view illustrating an example in which a user wears an optical modulator according to a second embodiment of the disclosure.

FIG. 2 is a view illustrating an example in which a user wears an optical modulator according to a second embodiment of the disclosure.

When light enters the eye of the patient 210 suffering from eye opacity (or clouded eye), the light may be scattered by the factor causing the eye opacity, failing to be precisely focused on the retina. Thus, the patient 210 sees external objects as blurred or cloudy.

To mitigate such symptom, an optical modulator 220 is disposed in front of the patient's eyes, specifically, in contact with the corneas. The optical modulator 220 is positioned in contact with the eyes of the patient 210 suffering from eye opacity, modulating the properties of the incident light depending on the degree of eye opacity. The optical modulator 220 may be shaped as a circle or ellipse which is appropriate for contacting the eye, and the optical modulator 220 may be implemented in the size of the eye (eyeball) to allow it appropriate to contact the eye. The optical modulator 220 may be implemented as, e.g., a contact lens. The properties of light modulated by the optical modulator 220 may include the phase, strength, or intensity of the light. The optical modulator 220 modulates the properties of light entering the eyes from ahead of the patient's eyes depending on the degree of eye opacity of the patient 210, allowing the modulated light to be normally focused on the retina while passing through the clouded eye, particularly, clouded lens.

Figure 3:
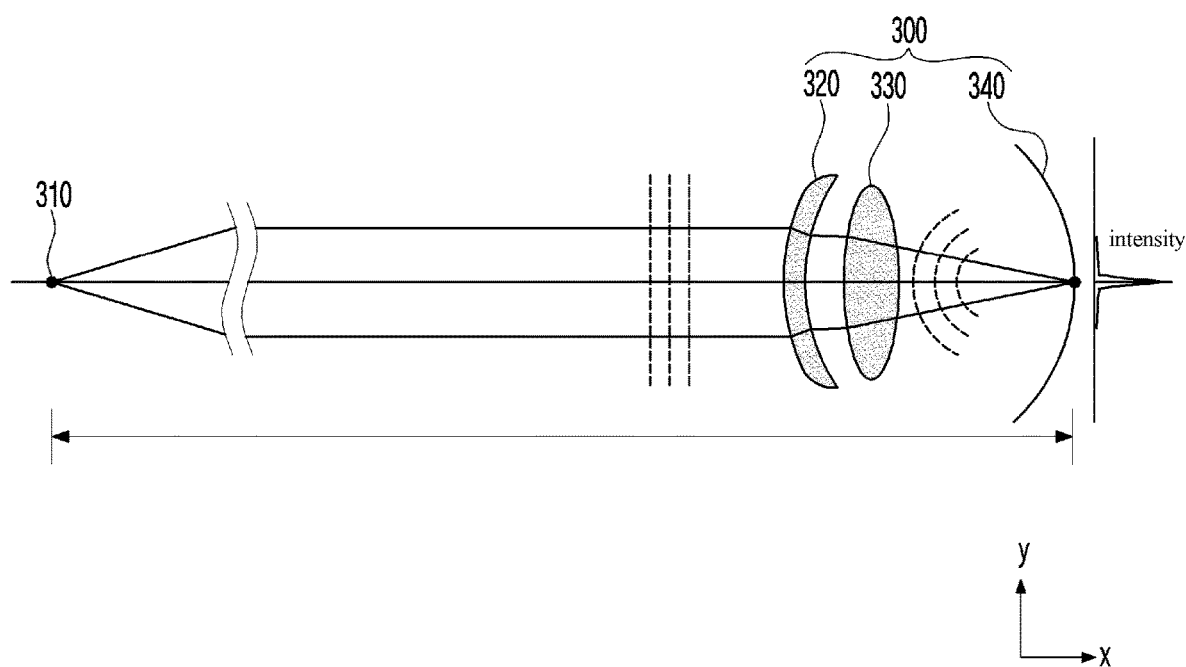
FIG. 3 is a view illustrating an example in which coherent short-wavelength collimated light rays enter an eye whose front segment is normal and are focused and the strength of the light rays on the retina as marked on a one-dimensional axis.
Figure 4:
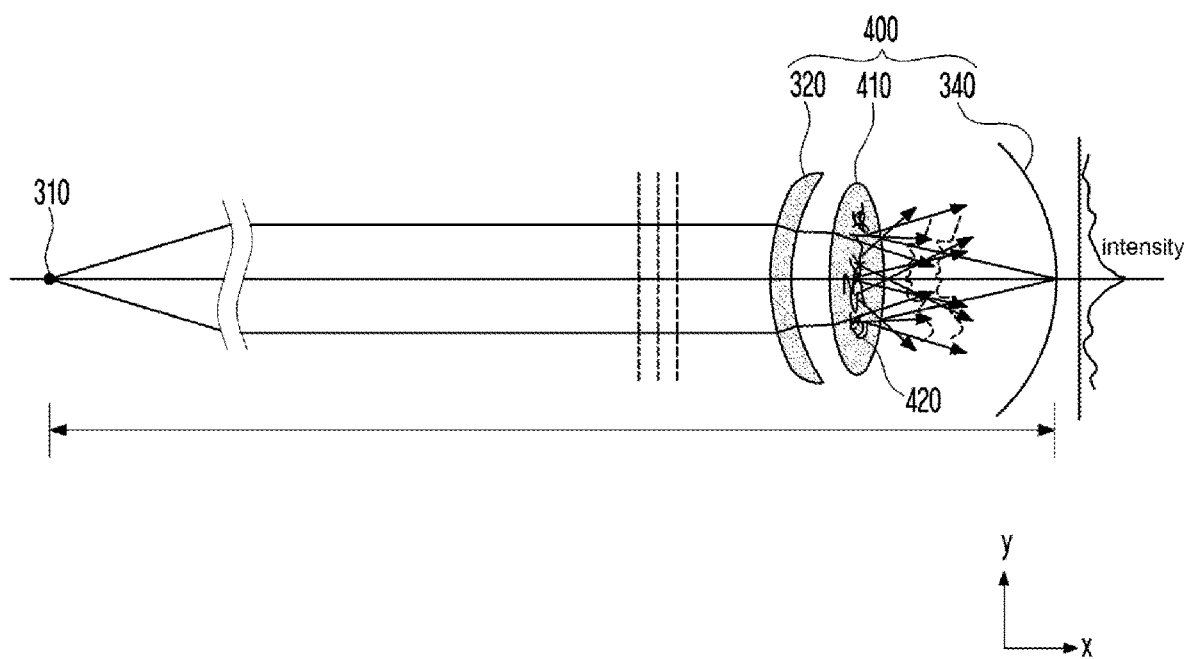
FIG. 4 is a view illustrating an example in which coherent short-wavelength collimated light rays enter an eye whose cornea or lens is clouded and are scattered and the strength of the scattered light rays focused on the retina as marked on a one-dimensional axis.

FIG. 3 is a view illustrating an example in which coherent short-wavelength collimated light rays enter an eye whose front segment is normal and are focused and the strength of the light rays on the retina as marked on a one-dimensional axis. FIG. 4 is a view illustrating an example in which coherent short-wavelength collimated light rays enter an eye whose cornea or lens is clouded and are scattered and the strength of the scattered light rays focused on the retina as marked on a one-dimensional axis.

Referring to FIG. 3, light rays reflected by an object 310 strike a normal eye 300 which has no eye opacity and are transferred in the form of spherical waves while passing through the cornea 320 and lens 330 and are then focused on the retina 340. Thus, a high intensity of light is detected in the center of the retina 340 and, as going off the center of the retina 340, a low intensity of light or almost no light is detected.

Referring to FIG. 4, the clouded eye 400 detects light in a different manner from that of the normal eye 300. Light rays reflected by an object 310 enter the eye 400 and pass through the cornea 320 and lens 410. The clouded eye 400 have foreign bodies 420 on the surface or inside of the lens 410, which scatter the light rays entering the lens 410. The light rays scattered by the foreign bodies 420 may have random properties (e.g., random phases and strengths) depending on the position and degree of the foreign bodies 420. The light rays scattered with the random properties may not properly be focused on the retina 340. A high intensity of light is detected in the center of the retina 340 and, although going off the center of the retina 340, a predetermined intensity of, or more, light may be irregularly detected. By such a nature, the patient with the clouded eye 400 may perceive the object 310 as blurred or cloudy.

Such a symptom may be addressed by placing an optical modulator 120 or 220 in front of the clouded eye 400. The modulation properties of the optical modulator 120 or 220 are detected and selected by an eye opacity reducing device 500 described below.

Figure 5:
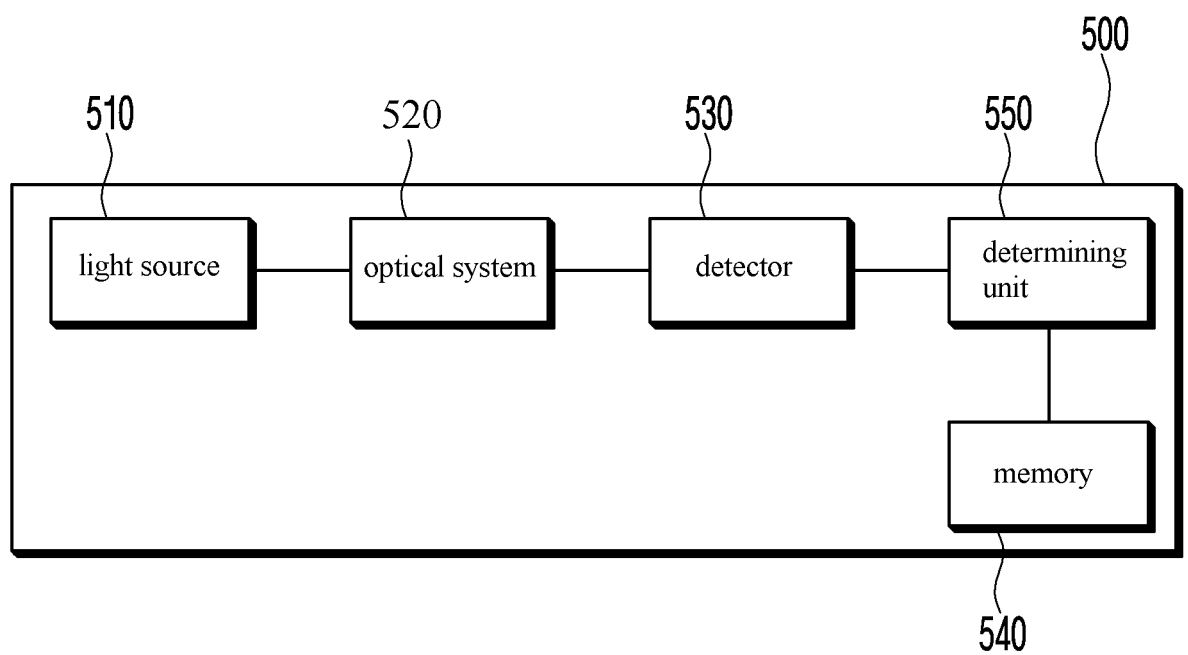
FIG. 5 is a block diagram illustrating a configuration of an eye opacity reducing device according to an embodiment of the disclosure.

FIG. 5 is a block diagram illustrating a configuration of an eye opacity reducing device according to an embodiment of the disclosure.

Referring to FIG. 5, an eye opacity reducing device 500 includes a light source 510, an optical system 520, a detector 530, a memory 540, and a determining unit 550.

The eye opacity reducing device 500 emits light to the eye and detects the degree of opacity of the eye by detecting information for interference (hereinafter, "interference information") between the light entering the eye and the light reflected by the retina. The eye opacity reducing device 500 detects the properties of interfering light when each of optical modulators with different modulation properties is positioned in front of or in contact with the eye to thereby detect the degree of eye opacity, thereby determining whether light modulated by the positioned optical modulator is optimal, and if optimal, select the optimal optical modulator. The eye opacity reducing device 500 may detect the properties of interfering light by emitting light to the real eye or a pseudo eye model similar to the real eye.

The light source 510 emits light to the optical system 520 for detecting the degree of eye opacity. The light source 510 emits light to the optical system 520, and the light is incident through the optical system 520 to the eye. The light emitted from the light source 510 may have a non-visible light wavelength range, e.g., a near-infrared wavelength range, in which the iris muscles of the front segment of the eye do not react. The light emitted from the light source 510 is incident through the optical system 520 to the eye and then passes through the inside of the eyeball to the retina. The light is then reflected by the retina. Among the light rays, some travelling to the opening of the iris, i.e., the pupil, need to exit the eyeball. When light is incident onto the eye and is then reflected out, the light emitted from the light source 510 interferes with the light reflected out of the eye, and the eye opacity reducing device 500 may detect information for the interference and quantify the degree of eye opacity. Thus, the light source 510 may emit a near-infrared wavelength range of light, which is not absorbed but reflected out after entering the eye. The light incident onto the eye passes through the iris 310, the lens 320, and the vitreous humor 410 and reaches the retina. Then, the light is reflected by the retina and exists the eye through the vitreous humor 410, the lens 320, and the iris 310. As such, light entering the eye may create an interference pattern according to the degree of eye opacity while passing through the components of the eye. Since light emitted from the light source 510 enters the eye via the optical system 520, the strength of the light from the light source 510 may be about 800 µJ which does not damage the retina.

The optical system 520 leads to interference between the light emitted from the light source 510 and the light reflected out the eye.

The optical system 520 induces interference between the light emitted from the light source 510 and the reflected out the eye, allowing the detector 530 and the determining unit 550 to measure the degree of eye opacity. The optical system 520 induces interference between the light entering the eye and the reflected light exiting the eye, generating interfering light. The detector 530 may detect the properties of the generated interfering light, and the determining unit 550 may analyze the detected properties of the interfering light to thereby detect the degree of eye opacity. For example, the eye, if normal, would not cause interference or produce such a form of information that collimated light and spherical waves interfere with each other. In contrast, the eye, if clouded, causes interference due to light ray pairs that correspond to coherent conditions. As such, the optical system 520 leads to interference between the light entering the eye and the light reflected inside the eye and exiting the eye, thereby generating interference information by which the degree of eye opacity may be detected.

The optical system 520 leads to interference only between the light emitted from the light source 510 and the light reflected out the eye using phase modulation. The optical system 520 modulates the phase of light so that the reflected light exiting the eye has a specific polarized direction. The optical system 520 may lead to interference only between light rays with the specific polarized direction among the light rays emitted from the light source 510 and the reflected light exiting the eye. As such, the optical system 520 allows for interference only between the light emitted from the light source 510 and the reflected light exiting the eye regardless of whether there is external light. The optical system is described below in greater detail with reference to FIGS. 6 and 7.

The detector 530 detects the interference information generated by the optical system 520. The detector 530 detects the interference information generated by the optical system 520, extract, e.g., the strength (or intensity) or phase of the interfering light, and quantify the degree of eye opacity. When the optical modulator 120 or 220 is not disposed in front of or in contact with the eye or, although disposed, it does not influence the properties of light passing therethrough, the detector 530 detects interference information and quantifies the degree of opacity of the eye regardless of the presence or absence of the optical modulator. In contrast, when the optical modulator 120 or 220 is disposed in front of (apart from) or in contact with the eye and influences the properties of light passing therethrough, the detector 530 detects interference information and measures the degree of opacity of the eye before which the optical modulator is disposed. Since the detector 530 detects the interference information, the target for detection may be the eye with no optical modulator disposed before or the eye with an optical modulator disposed before.

The memory 540 detects interference information for the normal eye in which there is no cloudiness and stores the interference information in the form of data. Typically, if normal, i.e., not clouded, the eye has no interference between the light entering the eye and the reflected light exiting the eye or partial interference between the collimated light and the spherical wave. The memory 540 stores interference information for the normal eye in which there is no cloudiness in the form of data.

The determining unit 550 compares the interference information detected by the detector 530 with the interference information stored in the memory 540, determining whether the optimal optical modulator has been disposed. The determining unit 550 compares the value detected for the property of interfering light generated from the eye with an optical modulator disposed before with the value detected for the property of interfering light for the normal eye, which is stored in the memory 540, thereby determining whether an error between the two detected values falls within a preset range. The determining unit 550 determines the error between the two detected values and determines that the optical modulator for which the error falls within the preset range, particularly the optical modulator for which the error is smallest, is the optimal optical modulator.

Since the eye opacity reducing device 500 is able to detect the degree of opacity of the clouded eye, the determining unit 550 may obtain the modulation property of the optical modulator which allows light to be properly focused in the clouded eye, corresponding to the degree of eye opacity. However, since all variables including variations (in refractive index) of the media through which light passes may not be reflected in obtaining the modulation property, although an ideal optical modulator is disposed, there may be made a difference from the interference information for the normal eye which is stored in the memory 540. To address such issue, the eye opacity reducing device 500 may detect interference information for a plurality of optical modulators with various modulation properties and determine whether the error between each detected interference information (value) and the detected value for the normal eye falls within the error range. The eye opacity reducing device 500 may perform detection and determination on the plurality of optical modulators with various modulation properties, thereby selecting the optimal optical modulator to the patient with the clouded eye.

Figure 6:
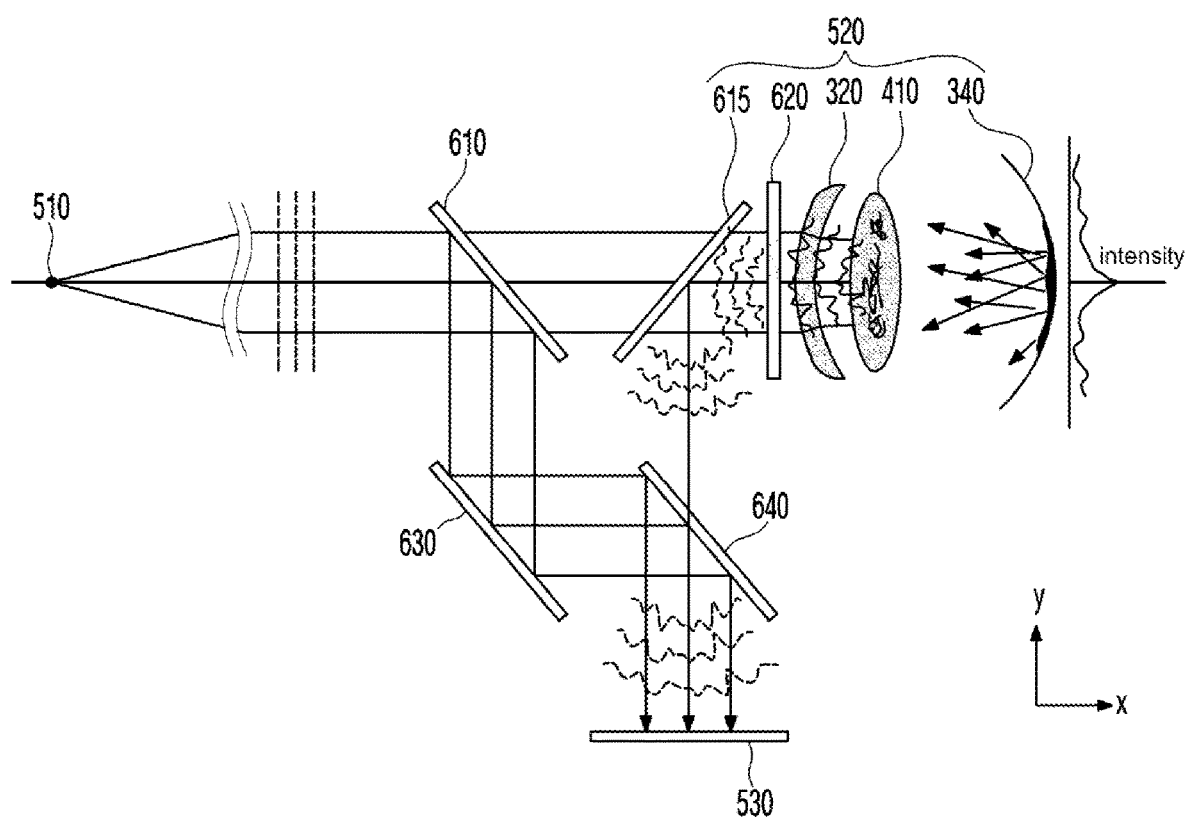
FIG. 6 is a view illustrating a process of obtaining interference information from a clouded eye by an eye opacity reducing device according to an embodiment of the disclosure.

FIG. 6 is a view illustrating a process of obtaining interference information from a clouded eye by an eye opacity reducing device according to an embodiment of the disclosure.

The light source 510 emits light to the optical system 520 for measuring the degree of eye opacity.

The optical system 520 leads to interference between the light emitted from the light source 510 and the light reflected out the eye. The optical system 520 includes a first polarizer 610, a second polarizer 615, a wave plate (e.g., a phase delay) 620, a mirror 630, and a half mirror 640.

The first polarizer 610 reflects only a preset polarization component of light emitted from the light source 510 and entering the eye to the mirror 630 while transmitting the rest of the light. The first polarizer 610 is disposed in the direction of reflecting the light emitted from the light source 510 to the mirror 630, reflecting only the preset polarization component of the light entering the eye while transmitting the rest of the light to the eye. For example, if the component the first polarizer 610 reflects is P-Pol, the P-Pol component of the light emitted from the light source 510 is reflected by the first polarizer 610 to the mirror 630, and the S-Pol component of the light passes through the first polarizer 610 to the eye. The first polarizer 610 may be implemented as an optical element, e.g., a wire grid polarizer (WGP), that reflects only a specific polarization component of incident light.

The second polarizer 615 is disposed between the first polarizer 610 and the eye, reflecting a preset polarization component of light to the half mirror 640. The second polarizer 615 may reflect the same component as the first polarizer 610. The second polarizer 615 is disposed in the direction of reflecting the light reflected by the eye to the half mirror 640, reflecting a preset polarization component of light to the half mirror 640. Since the preset polarization component of light striking the first polarizer 610 is reflected by the first polarizer 610, the light passing through the first polarizer 610 is incident through the second polarizer 615 to the eye (cornea and lens). The second polarizer 615 reflects the preset polarization component of light entering the eye and reflected out the eye to the half mirror 640.

The wave plate 620 is disposed between the second polarizer 615 and the eye, shifting the phase of light entering the eye or reflected light exiting the eye. The wave plate 620 may be implemented as an optical element with the property of delaying a specific wavelength of light by ¼ wavelength and shifts the phase of light passing therethrough by 45 degrees. The light incident through the second polarizer 615 to the eye is 45-degree phase-shifted while passing through the wave plate 620, and the light entering the eye and reflected out the eye is 45-degree phase-shifted while passing through the wave plate 620 before entering the second polarizer 615. Thus, if the polarization component of light incident through the second polarizer 615 to the eye is perpendicular to the preset polarization component, the polarization component of light reflected by the eye to the second polarizer 615 is phase-shifted to the preset polarization component while passing through the wave plate 620 two times. According to the position and phase shift property of the wave plate 620, the light emitted from the light source 510, passing through the first polarizer 610, the second polarizer 615, and the wave plate 620 to the eye, reflected by the eye, and then passing through the wave plate 620 has the same polarization component as the light reflected by the first polarizer 610, causing interference therebetween. In other words, the eye opacity reducing device 500 changes the polarization component of the light to be interfered with, thereby subjecting only light emitted from the device to interference.

The mirror 630 reflects the preset polarization component of light reflected by the first polarizer 610 to the half mirror 640. The light reflected by the first polarizer 610 and the light reflected by the second polarizer 615, when traveling along the same path, interfere with each other. However, since the polarizers 610 and 615 are disposed in different positions and reflect light in different directions, the light rays reflected by such polarizers 610 and 615 do not interfere with each other. The mirror 630 reflects the preset polarization component of light reflected by the first polarizer 610 to the half mirror 640 so that the light rays reflected by the two polarizers 610 and 615 may interfere with each other. The mirror 630 may be implemented as a dichroic mirror for fully reflecting the specific polarization component of light.

The half mirror 640 allows the preset polarization component of light reflected by the first polarizer 610 and the preset polarization component of light reflected by the second polarizer 615 to travel in the same direction, thus leading to interference therebetween. The half mirror 640 reflects the light reflected by the mirror 630 while transmitting the preset polarization component of light reflected by the second polarizer 615. Thus, the light rays interfere with each other while travelling along the same path. As described above, since the light rays have the same polarization component, they may interfere with each other. The light rays interfering with each other (simply, interfering light (rays)) while passing through the half mirror 640 are incident onto the determining unit 550, and the detector 530 performs detection.

Since no optical modulator is positioned ahead of the clouded eye 400, light is not normally focused on the retina 340 in the eye.

Figure 7:
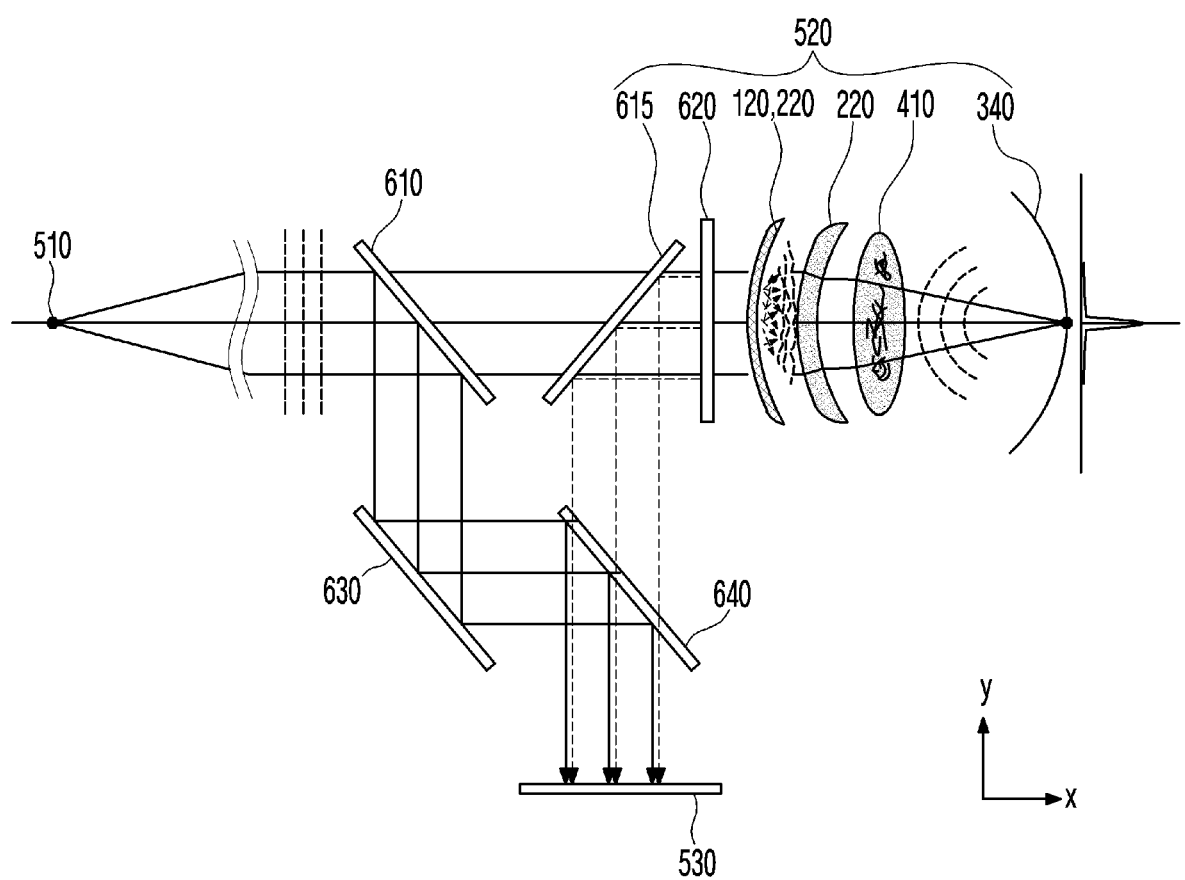
FIG. 7 is a view illustrating a process of measuring interference information by an eye opacity reducing device when an optical modulator according to the first embodiment or second embodiment is positioned in front of or in contact with the clouded eye, according to an embodiment of the disclosure.
Figure 8A:
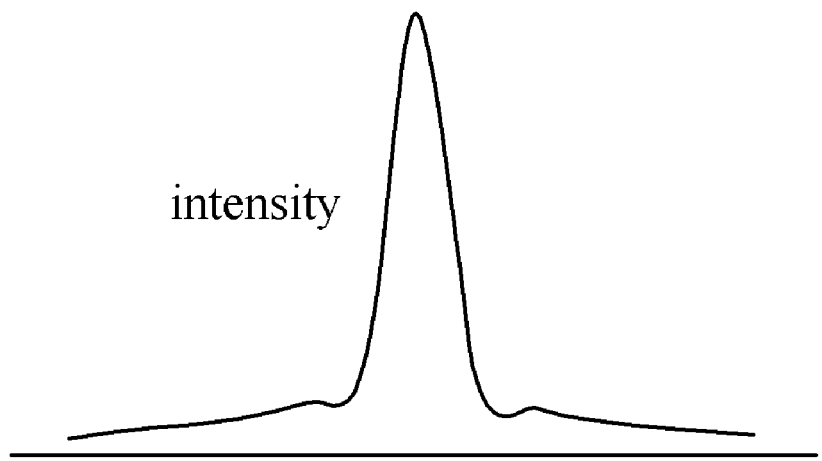
FIGS. 8A and 8B are views illustrating, on a one-dimensional axis, the distribution of light focused on the retina in a normal eye and in a clouded eye when an optical modulator according to the first or second embodiment is disposed, according to an embodiment of the disclosure.
Figure 8B:
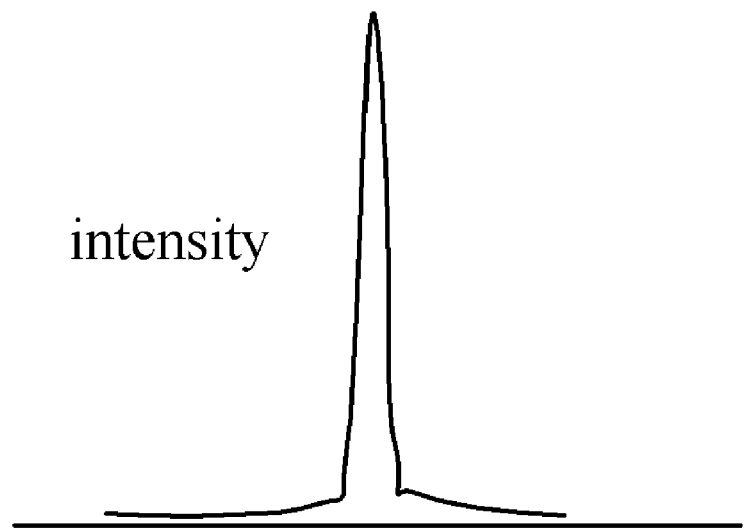

FIG. 7 is a view illustrating a process of measuring interference information by an eye opacity reducing device when an optical modulator according to the first embodiment or second embodiment is positioned in front of or in contact with the clouded eye, according to an embodiment of the disclosure. FIGS. 8A and 8B are views illustrating, on a one-dimensional axis, the distribution of light focused on the retina in a normal eye and in a clouded eye when an optical modulator according to the first or second embodiment is disposed, according to an embodiment of the disclosure.

Even where an optical modulator 120 or 220 is disposed in front of or in contact with the clouded eye 400, the eye opacity reducing device 500 creates interference using the optical system 520 and extracts interference information using the detector 530. The eye opacity reducing device 500 may quantify the degree of eye opacity from the detected value for the nature of the interfering light. The eye opacity reducing device 500 may compare the interference information for when the optical modulator 120 or 220 is disposed with the interference information for the normal eye stored in the memory 540, thereby identifying whether the optical modulator 120 or 220 is the optimal one.

FIG. 8A is a graph illustrating, on a one-dimensional axis, the strength distribution of light focused on the retina when the degree of eye opacity is corrected based on the interference information for the clouded eye, with a specific optical modulator disposed in front of or in contact with the eye. FIG. 8B is a graph illustrating, on a one-dimensional axis, the light strength distribution for the normal eye with no cloudiness, stored in the memory 540. Referring to FIG. 8A, the eye opacity reducing device 500 repeatedly generates light modulation patterns based on various pieces of interference information for eye opacity, providing the optical modulator by which interference may be minimized. This forms an environment that results in the smallest difference (i.e., smallest influence by light scattered due to cloudiness or opacity) between the strength distribution of light focused on the retina in the normal eye and the strength distribution of modulated light on the retina. The eye opacity reducing device 500 selects the optical modulator for which the difference between the two detected values falls within a preset error range, in particular, the optical modulator which leads to the smallest difference or error between the two detected values, as the optimal optical modulator.

Figure 9:
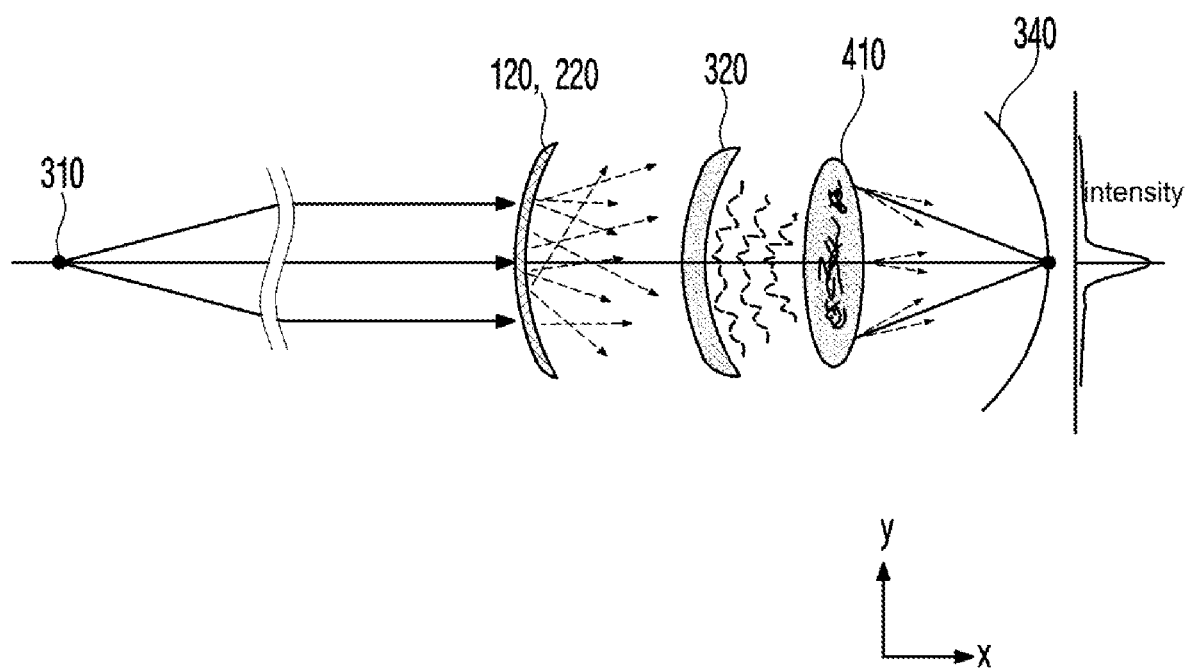
FIG. 9 is a view illustrating a process of correcting scattered light by providing inversely scattered light information about a clouded eye when an optical modulator according to the first or second embodiment is disposed and a result of the process, according to an embodiment of the disclosure.

FIG. 9 is a view illustrating a process of correcting scattered light by providing inversely scattered light information about a clouded eye when an optical modulator according to the first or second embodiment is disposed and a result of the process, according to an embodiment of the disclosure.

Where the optimal optical modulator 120 or 220 is disposed in front of or in contact with the clouded eye, the optimal optical modulator 120 or 220 modulates the properties of light to correspond to the degree of eye opacity. The property-modulated light passes through the cornea 310 and the lens 410 and is then precisely focused on the retina 340.

Figure 10:
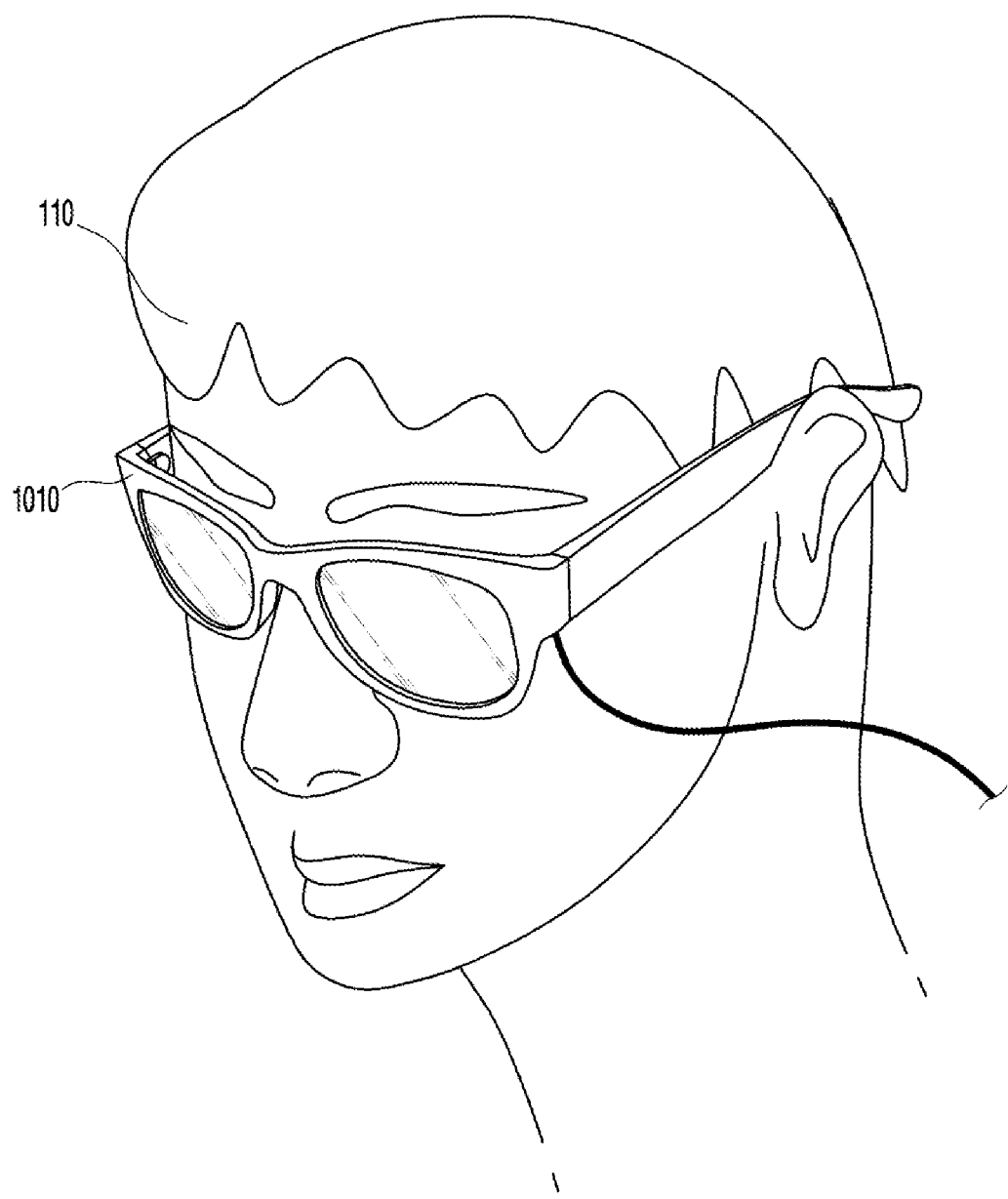
FIG. 10 is a perspective view illustrating an example product printed with an optical pattern determined from an optical modulator according to a third embodiment of the disclosure.

FIG. 10 is a perspective view illustrating an example product printed with an optical pattern determined from an optical modulator according to a third embodiment of the disclosure.

Like the optical modulator 120, an optical modulator 1010 modulates light in front of the eye of the patient 110 suffering from eye opacity, allowing the light entering the eye to precisely be focused on the retina. Further, the optical modulator 1010 senses the properties of the light entering the eye, allowing for modulation properties adaptively to the properties of light. As the optical modulator 1010 has the modulation properties adaptively to the properties of incident light, the patient 110 wearing the optical modulator 1010 may clearly see whatever property of light is incident in whatever environment.

Figure 11:
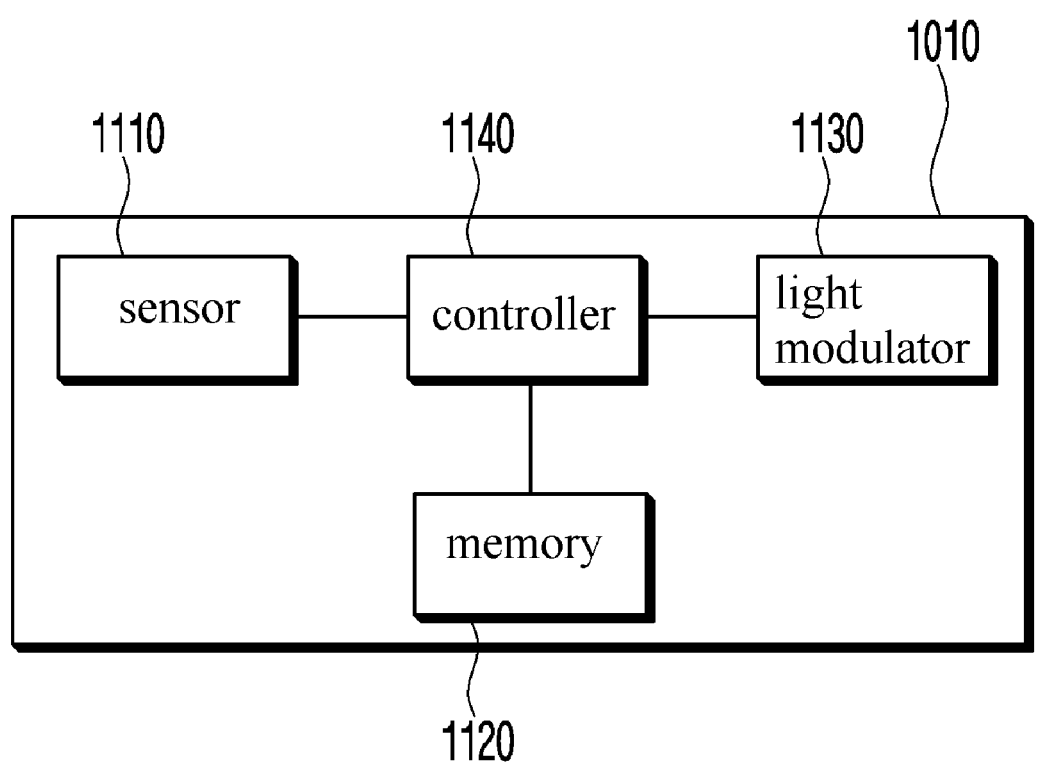
FIG. 11 is a block diagram illustrating a configuration of an optical modulator according to the third embodiment of the disclosure.

FIG. 11 is a block diagram illustrating a configuration of an optical modulator according to the third embodiment of the disclosure.

Referring to FIG. 11, according to the third embodiment, an optical modulator 1010 includes a sensor 1110, a memory 1120, a light modulator 1130, and a controller 1140.

The sensor 1110 senses the properties of light entering the eye. The properties of light sensed by the sensor 1110 include all or some of the phase, strength or intensity, and incident direction of light. The sensor 1110 senses the properties of light and transfers the sensed light properties to the controller 1140.

The memory 1120 stores the optimal modulation property of the light modulator corresponding to various light properties. The memory 1120 stores the optimal modulation property of the light modulator 1130 for each property of light entering the eye. As used herein, the phrase "optimal modulation property" means that when light with a specific property enters the eye, the modulation property of the light modulator with the closest detected value to the detected value for the property of interfering light for the normal eye. The memory 1120 matches the property of each light ray entering the eye with the optimal modulation property of the light modulator and stores them.

The light modulator 1130 is disposed in front of the eye to modulate the properties of light. The light modulator 1130 may play the same role as the optical modulator 120 but, unlike the optical modulator 120, the light modulator 1130 may actively vary the modulation property. For example, the light modulator 1130 may be implemented as an acousto-optical modulator (AOM) or electro-optic modulator (EOM) capable of actively varying the modulation property. Since the optical modulator 120 has only predetermined modulation properties, detection of the properties of interfering light is performed with various optical modulators disposed so as to place the optimal optical modulator. In contrast, the light modulator 1130 may receive input from the outside and actively vary the modulation property. The light modulator 1130 receives power corresponding to each modulation property from the controller 1140 and varies the modulation property according to the received power.

The controller 1140 analyzes the property of light sensed by the sensor 1110 and controls the light modulator 1130 to have the optimal modulation property. The controller 1140 analyzes the property of light sensed by the sensor 1110 and selects the optimal modulation property (of the light modulator) corresponding to the analyzed light property from the memory 1120. The controller 1140 applies power (e.g., current) corresponding to the selected modulation property to the light modulator 1130, thereby controlling the light modulator 1130 to have the selected modulation property. Thus, the optical modulator 1010 may vary the modulation property for incident light in real-time, thereby performing optical modulation optimal to the patient 110.

Figure 12:
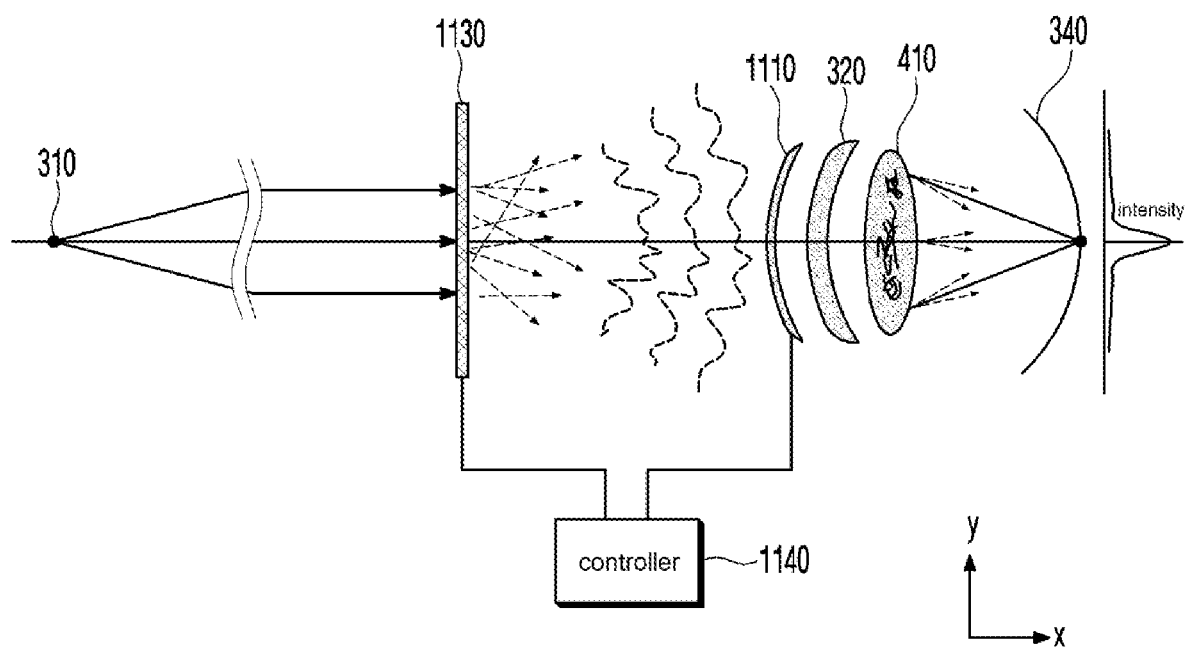
FIG. 12 is a view illustrating a process of forming an optimal inversely scattered light pattern in a clouded eye when an optical modulator according to the third embodiment is disposed and the strength of light focused on the retina, with the scattered light is minimized by the final pattern, as marked on a one-dimensional axis.

FIG. 12 is a view illustrating a process of forming an optimal inversely scattered light pattern in a clouded eye when an optical modulator according to the third embodiment is disposed and the strength of light focused on the retina, with the scattered light is minimized by the final pattern, as marked on a one-dimensional axis.

The sensor 1110 is disposed in front of the eye and senses the properties of light entering the eye. The sensor 1110 transfers the sensed value for the light property to the controller 1140, and the controller 1140 selects the optimal modulation property corresponding to the received light property. The controller 1140 controls the light modulator 1130 to have the optimal modulation property as selected, and the light modulator 1130 has the modulation property under the control of the controller 1140.

As having the optimal optical modulation property for incident light, the light modulator 1130 may perform optical modulation optimal to the patient 110.

Figure 13:
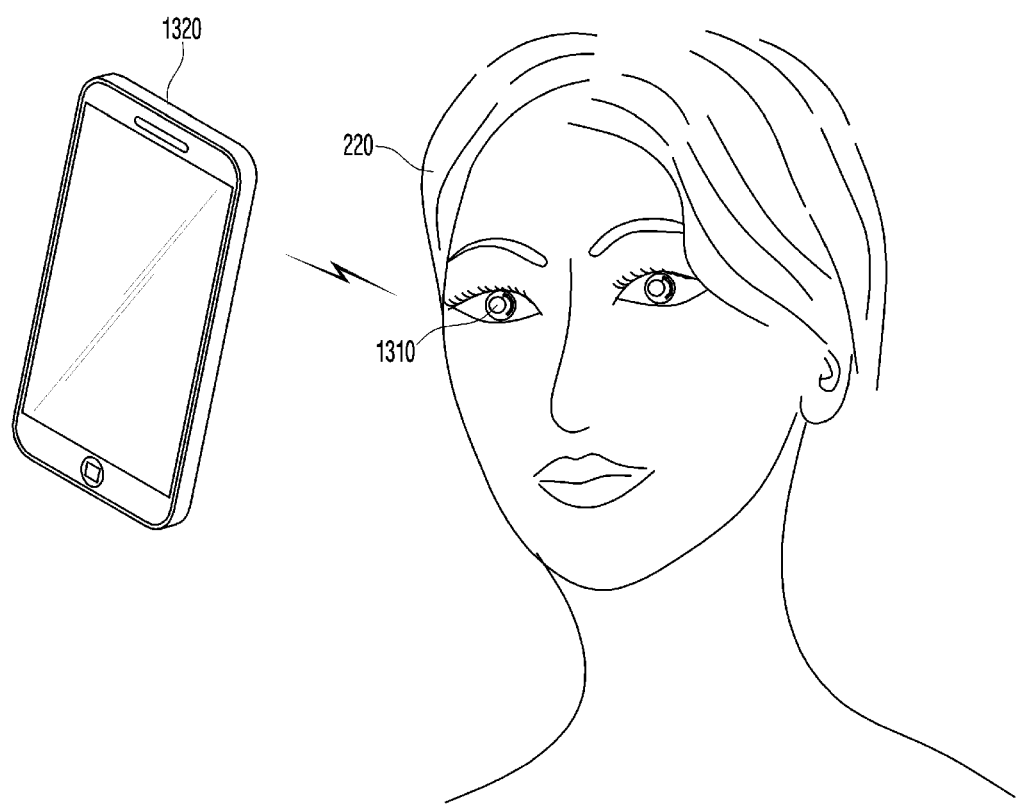
FIG. 13 is a view illustrating an example in which a user wears an optical modulator according to a fourth embodiment of the disclosure.

FIG. 13 is a view illustrating an example in which a user wears an optical modulator according to a fourth embodiment of the disclosure.

Like the optical modulator 220, an optical modulator 1310 modulates light in front of the eye of the patient 210 suffering from eye opacity, allowing the light entering the eye to precisely be focused on the retina. The optical modulator 1310 receives a control signal for the optical modulation property from an outside (e.g., a terminal 1320) and actively varies the modulation property according to the control signal. The patient 210 transmits the control signal for the optical modulation property to the optical modulator 1310 via the terminal 1320. The optical modulator 1310 varies the modulation property according to the control signal so that the patient 210 may set the optical modulator 1310 to have the optimal modulation property depending on his symptom.

The terminal 1320 receives the control signal for optical modulation property for the optical modulator 1310 from the patient 210 and transmits the control signal to the optical modulator 1310. The terminal 1320 transmits or receives signals to/from the optical modulator 1310 via wireless communication. The patient 210 may input a control signal for optical modulation property to the terminal 1320 to change the optical modulation property of his wearing optical modulator 1310, and the terminal 1320 transmits the received control signal for optical modulation property to the optical modulator 1310 via wireless communication. Thus, the patient 210 may vary the optical modulation property of his wearing optical modulator 1310 simply using the terminal 1320.

Figure 14:
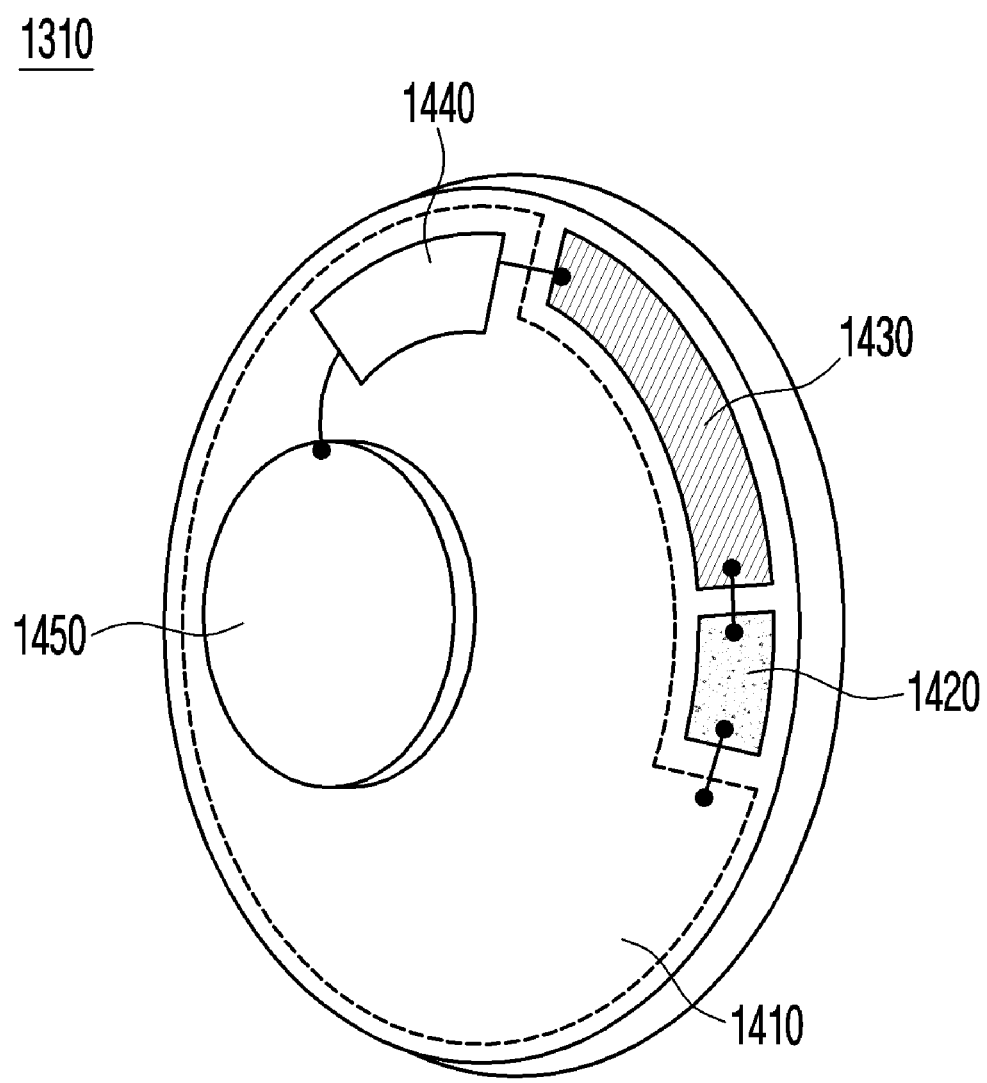
FIG. 14 is a view illustrating a configuration of an optical modulator according to the fourth embodiment of the disclosure.

FIG. 14 is a view illustrating a configuration of an optical modulator according to the fourth embodiment of the disclosure.

Referring to FIG. 14, according to the fourth embodiment, an optical modulator 1310 includes a battery 1420, a communication unit 1430 (e.g., a transceiver), a control/memory unit 1440, an light modulator 1450.

The optical modulator 1310 is disposed in front of or in contact with the eye, e.g., the cornea of the eye as described above. Like the optical modulator 220, the optical modulator 1310 may be shaped as a circle or ellipse appropriate to contact the eye. The rest of the optical modulator 1310 except for the components 1420 to 1450 may be implemented as a transparent solar cell 1410. The optical modulator 1310 contacts the eye and thus its size needs to be limited. The optical modulator 1310 includes power-consuming components such as the communication unit 1430 and the control/memory unit 1440. To address these issues, the rest of the optical modulator 1310 is implemented as the solar cell 1410. The optical modulator 1310 converts light entering the eye into electric energy using the solar cell 1410 and stores the electric energy in the battery 1420.

The battery 1420 stores the electric energy produced by the solar cell 1410. The battery 1420 stores electric energy obtained by the solar cell 1410 and provides power necessary for operation of each component 1430 to 1450 in the optical modulator 1310.

The communication unit 1430 wirelessly communicates with the terminal 1320 and receives a control signal for optical modulation property. As described above, the patient 210 transmits the control signal for optical modulation property to the optical modulator 1310 using the terminal 1320, and the communication unit 1430 receives the control signal and transfers the control signal to the control/memory unit 1440. The communication unit 1430 receives the control signal from the terminal 1320 via various types of wireless communication, e.g., Bluetooth, Wi-Fi, beacon, or Zigbee.

The control/memory unit 1440 analyzes the control signal received from the communication unit 1430 and controls the optical modulation property of the light modulator 1450 according to the control signal. The control/memory unit 1440 analyzes the control signal for the optical modulation property and controls the whole or part of the light modulator 1450 to have the modulation property according to the control signal. The control/memory unit 1440 varies the modulation property of part of the light modulator 1450 according to the control signal so that only light entering the part is modulated, or the control/memory unit 1440 may vary the modulation property of the whole light modulator 1450 according to the control signal.

The light modulator 1450 is disposed on the eye to modulate the properties of light. The light modulator 1450 may play the same role as the optical modulator 220 but, unlike the optical modulator 220, the light modulator 1130 may actively vary the modulation property. For example, the light modulator 1450 may be implemented as a liquid crystal (LC), an acousto-optical modulator (AOM) or electro-optic modulator (EOM) capable of actively varying the modulation property. The light modulator 1450 has a grating structure. The light modulator 1450 may vary the property of light by changing the shape or period of the grating. The light modulator 1450 varies, e.g., the shape or period of the grating of the whole or part of the light modulator 1450 under the control of the control/memory unit 1440, thereby changing the property of modulated light. Since the optical modulator 220 has only predetermined modulation properties, detection of the properties of interfering light is performed with various optical modulators disposed so as to place the optimal optical modulator. In contrast, the light modulator 1450 may actively vary the modulation property under the control of the control/memory unit 1440.

Figure 15:
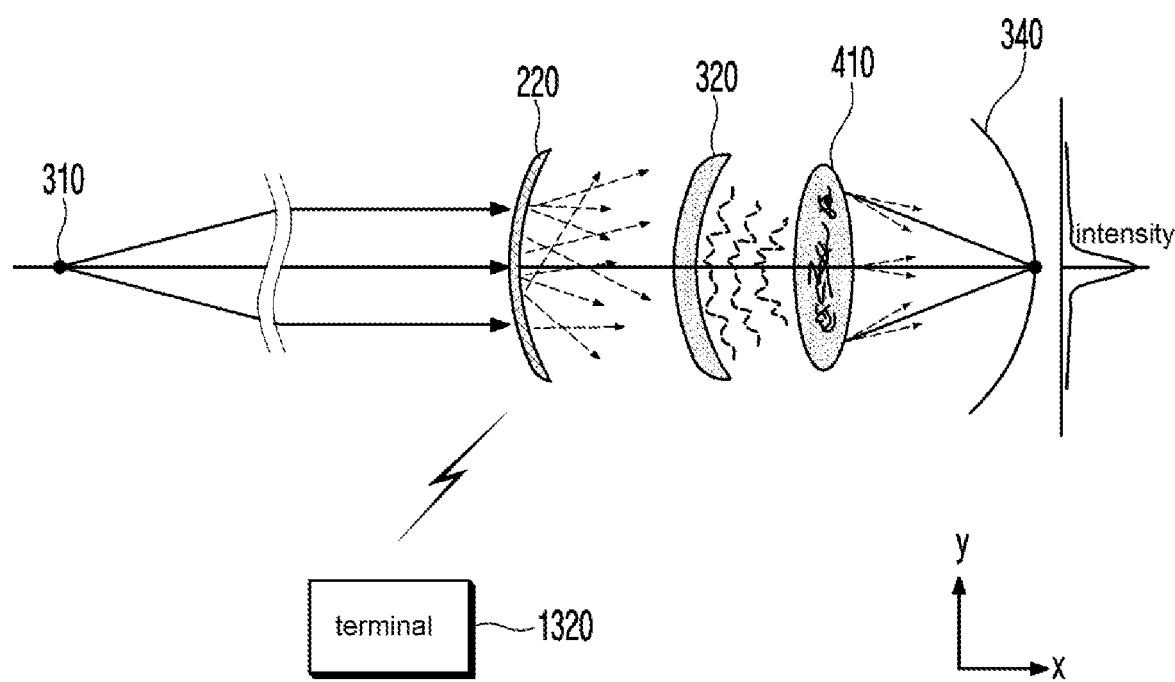
FIG. 15 is a view illustrating a process of forming an optimal inversely scattered light pattern in a clouded eye when an optical modulator according to the fourth embodiment is disposed and the strength of light focused on the retina, with the scattered light is minimized by the final pattern, as marked on a one-dimensional axis.

FIG. 15 is a view illustrating a process of forming an optimal inversely scattered light pattern in a clouded eye when an optical modulator according to the fourth embodiment is disposed and the strength of light focused on the retina, with the scattered light is minimized by the final pattern, as marked on a one-dimensional axis.

The light modulator 1450 has the optical modulation property according to the control signal received from the terminal 1320. Thus, the light modulator 1450 may perform optical modulation optimal to the patient 210.

The optical modulator described above in connection with FIGS. 1 to 15 may be implemented not as a device or apparatus but as an optical modulation pattern formed by the above-described measurement and correction and attached to an optical device.

The optical modulator 220 described above in connection with FIGS. 2 to 9 or the light modulator 1450 in the optical modulator 1310 described above in connection with FIGS. 13 to 15 may include a dye (not shown) The dye (not shown) may be used to compensate for red/green color blindness (or color weakness) or blue/yellow color blindness (or color weakness). Conventionally, such dyes are contained in or applied to, e.g., glasses worn on the eye. However, the dye is exposed and noticeable to others, causing the patient to feel uncomfortable. The optical modulator 220 or 1310 is disposed on (in contact with) the eye, is as small as the pupil, and is thus seldom exposed to the outside. Thus, inconvenience the patient wearing the optical modulator may feel may be minimized.

Figure 16:
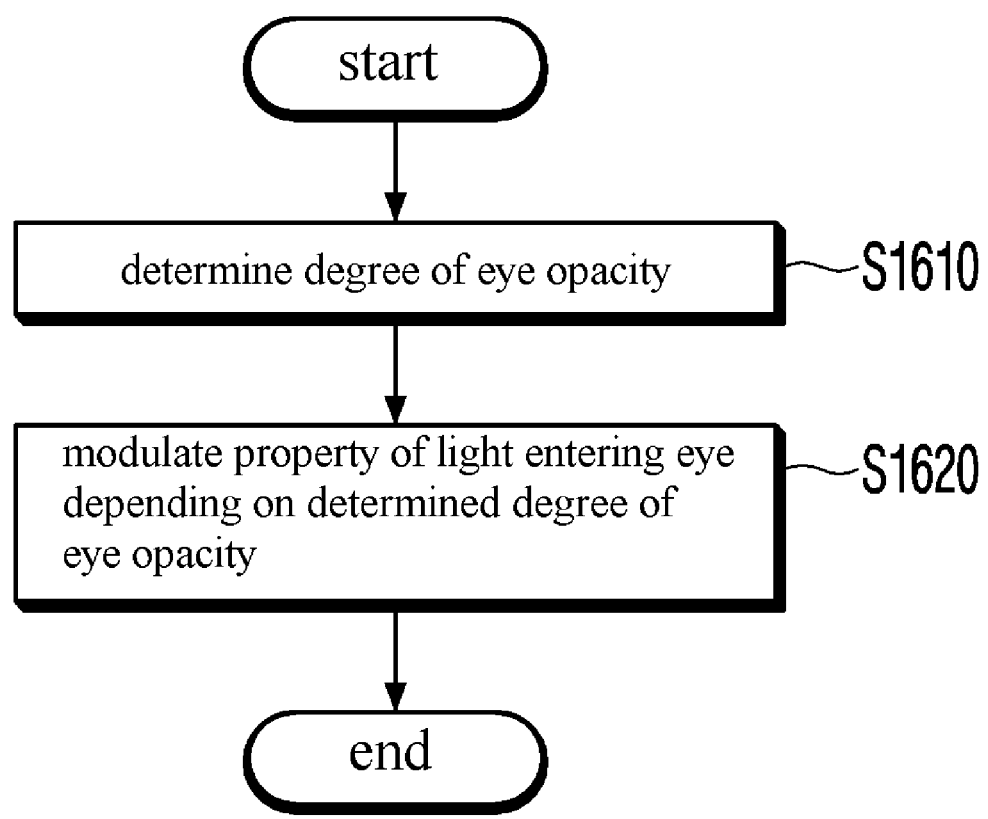
FIG. 16 is a flowchart illustrating a method of modulating light by an optical modulator according to the first or second embodiment, according to an embodiment of the disclosure.

FIG. 16 is a flowchart illustrating a method of modulating light by an optical modulator according to the first or second embodiment, according to an embodiment of the disclosure.

The eye opacity reducing device 500 determines the degree of eye opacity (S1610). The eye opacity reducing device 500 analyzes interference information and quantifies the degree of eye opacity.

The optical modulator 120 or 220 modulates the property of light entering the eye depending on the determined degree of eye opacity (S1620). Depending on the degree of eye opacity, the optical modulator 120 or 220 modulates the property of light entering the eye as optimal. Thus, the light may be focused in the eye with a specific degree of eye opacity.

Figure 17:
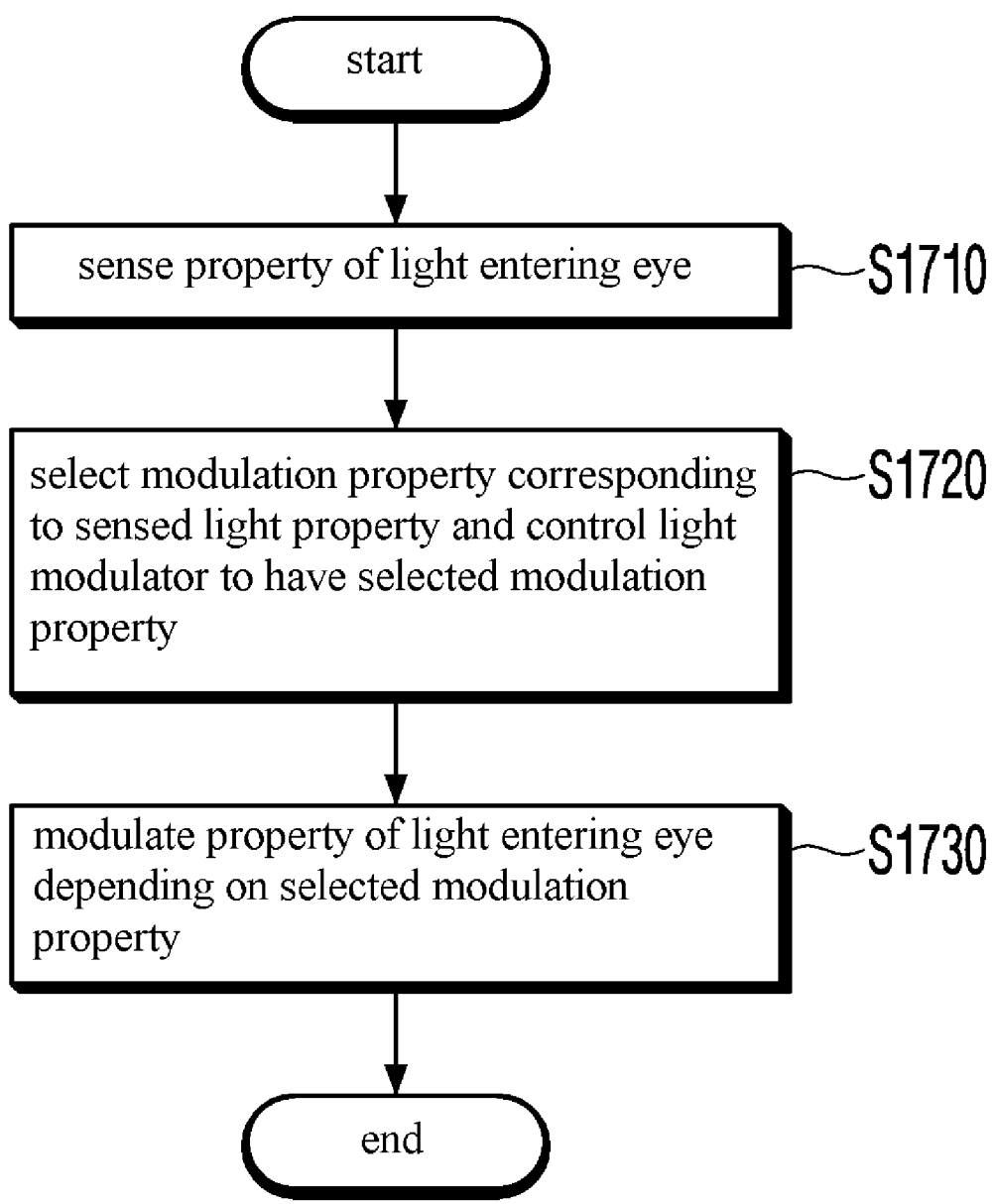
FIG. 17 is a flowchart illustrating a method of modulating light by an optical modulator according to the third embodiment, according to an embodiment of the disclosure.

FIG. 17 is a flowchart illustrating a method of modulating light by an optical modulator according to the third embodiment, according to an embodiment of the disclosure.

The optical modulator 1010 senses the property of light entering the eye (S1710).

The optical modulator 1010 selects the modulation property corresponding to the sensed light property and controls the light modulator to have the selected modulation property (S1720).

The optical modulator 1010 modulates the property of light entering the eye depending on the selected modulation property (S1730).

Figure 18:
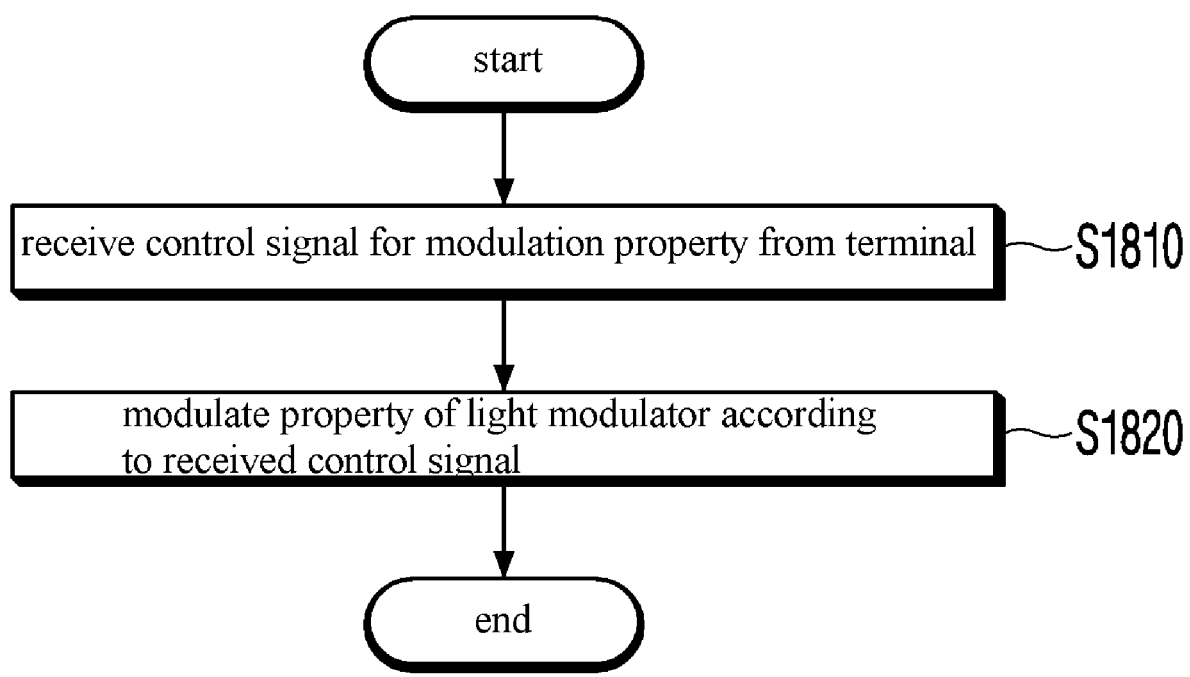
FIG. 18 is a flowchart illustrating a method of modulating light by an optical modulator according to the fourth embodiment, according to an embodiment of the disclosure.

FIG. 18 is a flowchart illustrating a method of modulating light by an optical modulator according to the fourth embodiment, according to an embodiment of the disclosure.

The optical modulator 1310 receives a control signal for modulation property from the terminal 1320 (S1810).

The optical modulator 1310 modulates the property of the light modulator according to the received control signal (S1820).

Figure 19:
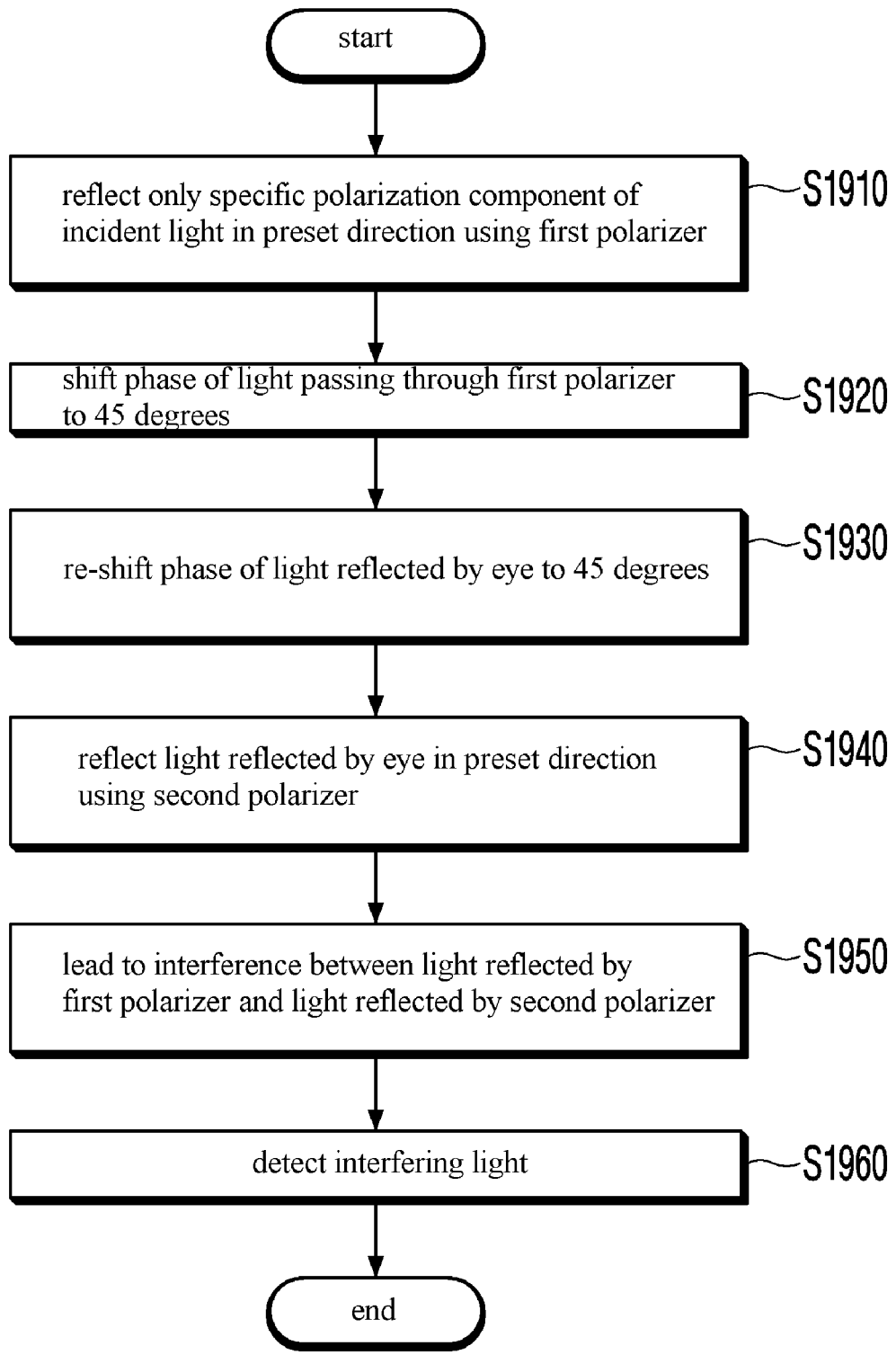
FIG. 19 is a flowchart illustrating a method of measuring interference information by an eye opacity reducing device according to an embodiment of the disclosure.

FIG. 19 is a flowchart illustrating a method of measuring interference information by an eye opacity reducing device according to an embodiment of the disclosure.

The eye opacity reducing device 500 reflects only a specific polarization component of incident light in a preset direction using a first polarizer (S1910). For example, the first polarizer 610 reflects a preset polarization component of light in the preset direction while transmitting the remaining polarization component of light.

The eye opacity reducing device 500 shifts the phase of the light passing through the first polarizer to 45 degrees (S1920). For example, the wave plate 620 shifts the phase of the light passing through the first polarizer to 45 degrees and then allows the phase-shifted light to enter the eye.

The eye opacity reducing device 500 again shifts the phase of the light reflected by the eye to 45 degrees (S1930). For example, the wave plate 620 again shifts the phase of the light reflected by the eye to 45 degrees. Thus, the polarization component of light reflected by the eye becomes identical to the polarization component reflected by the first polarizer 610.

The eye opacity reducing device 500 reflects the light reflected by the eye in a preset direction using the second polarizer (S1940). The second polarizer 615 reflects only the same polarization component as the first polarizer 610. Since the polarization component of light reflected by the eye is rendered to be identical to the polarization component reflected by the first polarizer 610 by the wave plate 620, the second polarizer 615 reflects the light reflected by the eye in the preset direction.

The eye opacity reducing device 500 leads to interference between the light reflected by the first polarizer 610 and the light reflected by the second polarizer 615 (S1950). The eye opacity reducing device 500 enables the light reflected by the first polarizer 610 and the light reflected by the second polarizer 615 to travel in the same direction using the mirror 630 and the half mirror 640, thereby inducing interference between the two light rays.

The eye opacity reducing device 500 detects interfering light (S1960). The eye opacity reducing device 500 receives the interfering light and detects the properties of the interfering light.

Figure 20:
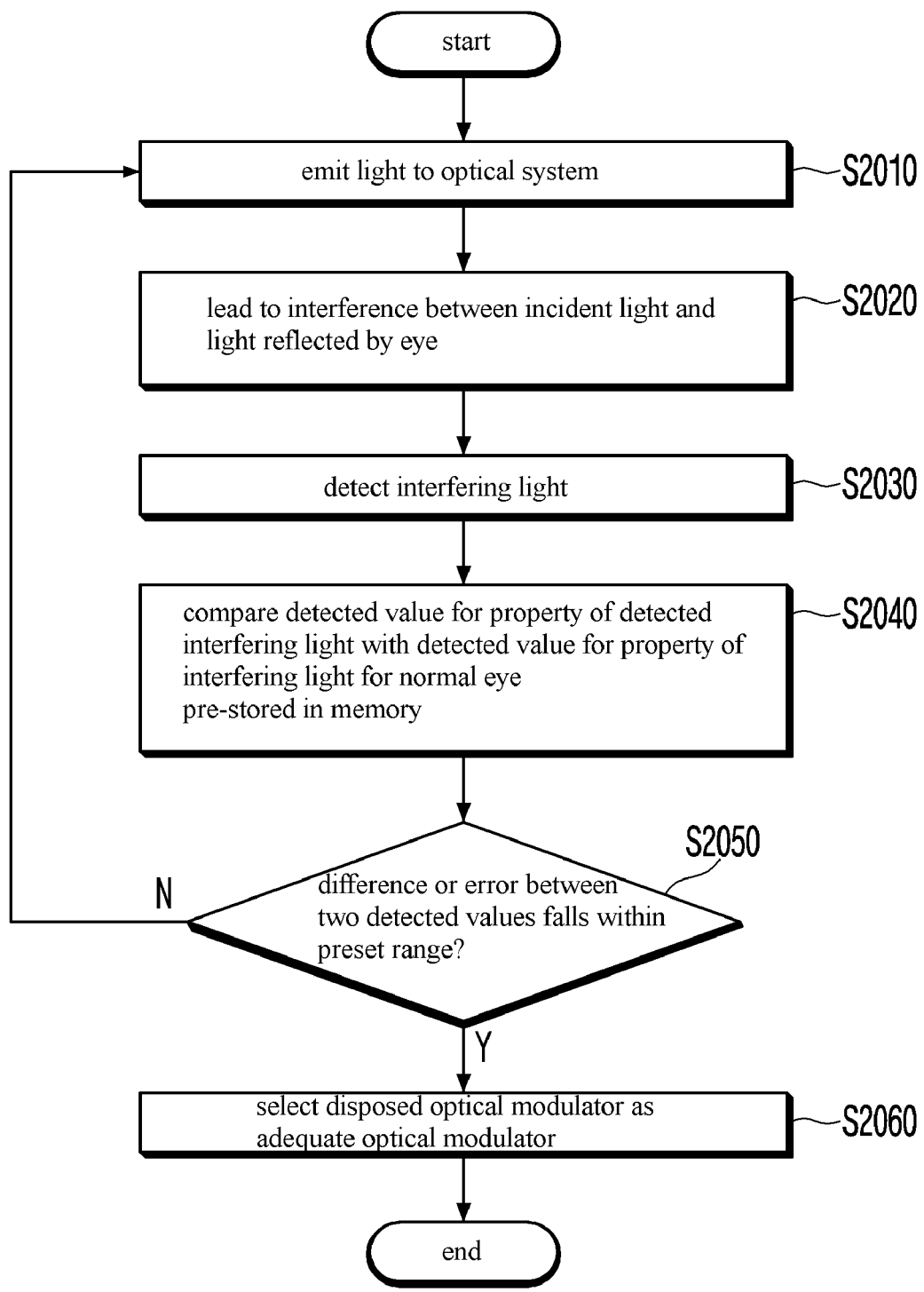
FIG. 20 is a flowchart illustrating a method of selecting an optimal optical modulator by an eye opacity reducing device according to an embodiment of the disclosure.

FIG. 20 is a flowchart illustrating a method of selecting an optimal optical modulator by an eye opacity reducing device according to an embodiment of the disclosure.

The light source 510 emits light to the optical system 520 (S2010).

The optical system 520 leads to interference between the incident light and the light reflected by the eye (S2020).

The detector 530 detects interfering light (S2030).

The determining unit 550 compares a detected value for the property of the detected interfering light with a detected value for the property of interfering light for the normal eye pre-stored in the memory 1120 (S2040).

The determining unit 550 determines whether a difference or error between the two detected values falls within a preset range (S2050).

If the error between the two detected values falls within the preset range, the determining unit 550 selects the disposed optical modulator as an adequate optical modulator (S2060).

Unless the error between the two detected values is within the preset range, the eye opacity reducing device 500 repeats the above-described steps or operations for other optical modulators.

Although FIGS. 16 to 20 illustrate that the steps are sequentially performed, this merely provides an embodiment of the disclosure. It would readily be appreciated by a skilled artisan that the steps of FIGS. 16 to 20 are not limited to the order shown but may rather be performed in a different order, one or more of the steps may simultaneously be performed, or other various modifications or changes may be made thereto without departing from the scope of the disclosure The steps or processes described above in connection with FIGS. 16 to 20 may be implemented as computer-readable code in a recording medium. The computer-readable recording medium includes all types of recording devices storing data readable by a computer system. The computer-readable recording medium includes a storage medium, such as a magnetic storage medium (e.g., a ROM, a floppy disk, or a hard disk) or an optical reading medium (e.g., a CD-ROM or a DVD). Further, the computer-readable recording medium may be distributed to computer systems connected via a network, and computer-readable codes may be stored and executed in a distributed manner.

The above-described embodiments are merely examples, and it will be appreciated by one of ordinary skill in the art various changes may be made thereto without departing from the scope of the disclosure. Accordingly, the embodiments set forth herein are provided for illustrative purposes, but not to limit the scope of the disclosure, and should be appreciated that the scope of the disclosure is not limited by the embodiments. The scope of the disclosure should be construed by the following claims, and all technical spirits within equivalents thereof should be interpreted to belong to the scope of the disclosure.

What is claimed is:
1. An optical modulator, comprising:
a sensor sensing a property of light entering an eye and a property of light reflected by the eye;
a memory storing the sensed property of each light ray and an optimal modulation light property of a light modulator according to the property of the light ray, with the property of the light matched with the optimal modulation light property;
a controller analyzing the property of the light sensed by the sensor, selecting the optimal modulation light prop- erty of the light modulator in the memory, and controlling the light modulator to have the selected modulation light property; and the light modulator having a modulation light property according to control of the controller and modulating the property of the light entering the eye, which is scattered in the eye, to form an inversely scattered light pattern, thereby allowing the light entering the eye to be focused on the retina, wherein the optimal modulation light property of the light modulator means that when light with a predetermined property enters the eye, the modulation light property of the light modulator has the closest detected value to the detected value for the property of interfering light for a normal eye in which there is no cloudiness, wherein the modulation light property includes a phase, strength, or intensity of the light, and wherein the light entering the eye interferes with the light reflected out of the eye, and the interfering light creates an interference pattern according to the degree of eye opacity.

2. The optical modulator of claim 1, wherein the property of the light includes a phase of the light, a strength of the light, or an incident direction of the light.

3. The optical modulator of claim 1, wherein the sensor and the light modulator are disposed in front of the eye along a direction in which the light enters the eye.

4. The optical modulator of claim 1, wherein the controller controls the modulation light property of the light modulator by transferring power corresponding to the modulation light property of the light modulator to the light modulator.

5. A method of modulating light, comprising:
detecting a property of light entering an eye and a property of light reflected by the eye;
analyzing the property of the light detected by the sensor to select an optimal modulation light property of a light modulator according to the detected property;
controlling the light modulator to have the selected modulation light property; and
modulating the property of the light entering the eye, which is scattered in the eye, to form an inversely scattered light pattern, thereby allowing the light entering the eye to be focused on the retina,
wherein the optimal modulation light property of the light modulator means that when light with a predetermined property enters the eye, the modulation light property of the light modulator has the closest detected value to the detected value for the property of interfering light for a normal eye in which there is no cloudiness,
wherein the modulation light property includes a phase, strength, or intensity of the light, and
wherein the light entering the eye interferes with the light reflected out of the eye, and the interfering light creates an interference pattern according to the degree of eye opacity.

6. The method of claim 5, wherein the property of the light includes a phase of the light, a strength of the light, or an incident direction of the light.

7. The method of claim 5, wherein the modulation light property of the light modulator is controlled by transferring power corresponding to the modulation light property of the light modulator to the light modulator.

* * * * *